US009334542B2

(12) United States Patent
Cummings et al.

(10) Patent No.: US 9,334,542 B2
(45) Date of Patent: May 10, 2016

(54) **COMPOSITIONS AND METHODS FOR DETECTION OF MICROORGANISMS OF THE *MYCOBACTERIUM AVIUM* COMPLEX EXCLUDING *MYCOBACTERIUM AVIUM PARATUBERCULOSIS***

(71) Applicant: LIFE TECHNOLOGIES CORPORATION, Carlsbad, CA (US)

(72) Inventors: Craig Cummings, Pacifica, CA (US); Pius Brzoska, Woodside, CA (US); Angela Burrell, Austin, TX (US); Catherine O'Connell, Austin, TX (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 173 days.

(21) Appl. No.: 13/785,531

(22) Filed: Mar. 5, 2013

(65) Prior Publication Data

US 2013/0260375 A1 Oct. 3, 2013

Related U.S. Application Data

(60) Provisional application No. 61/619,236, filed on Apr. 2, 2012.

(51) Int. Cl.
*C12P 19/34* (2006.01)
*C12Q 1/68* (2006.01)

(52) U.S. Cl.
CPC .......... *C12Q 1/689* (2013.01); *C12Q 2600/112* (2013.01)

(58) Field of Classification Search
None
See application file for complete search history.

(56) References Cited

U.S. PATENT DOCUMENTS

| 7,108,968 B2 * | 9/2006 | Gingeras et al. ............. 435/6.15 |
| 2007/0042383 A1 | 2/2007 | Kapur et al. |
| 2007/0105167 A1 * | 5/2007 | Ausubel et al. ............. 435/7.32 |
| 2013/0260374 A1 | 10/2013 | Ji et al. |

FOREIGN PATENT DOCUMENTS

| EP | 1371985 | 12/2003 |
| WO | WO2008/119332 | 10/2008 |
| WO | WO2013/151647 | 10/2013 |
| WO | WO2013/151648 | 10/2013 |

OTHER PUBLICATIONS

Ravva, S. et al., "Real-time quantitative PCR detection of *Mycobacterium avium* subsp. *paratuberculosis* and differentiation from other mycobacteria using SYBR Green and TaqMan assays", *Journal of Microbiological Methods*, vol. 63, 2005, pp. 305-317.
Stratagene Gene Characterization Kits 1988, pp. 38-39.
Alvarez et al., "Genetic Diversity of *Mycobacterium avium* Isolates Recovered from Clinical Samples and from the Environment: Molecular Characterization for Diagnostics Purposes", *Journal of Clinical Microbiology*, vol. 46, No. 4, Feb. 13, 2008, 1246-1251.
Bartos et al., "Identification of members of *Mycobaterium avium* species by Accu-Probes, serotyping, and single IS900, IS901, IS1245 and IS901-flanking region PCR with internal standards", *Journal Microbiological Methods*, vol. 64, No. 3, 2006, 333-345.
Cayrou et al., "Genotyping of *Mycobacterium avium* complex organisms using multispacer sequence typing", *Microbiology*, vol. 156, No. 3, Mar. 1, 2010, 687-694.
Covert et al., "Occurrence of nontuberculous mycobacteria in environmental samples", *Applied and Environmental Microbiology*, vol. 65, No. 5, Jun. 1999, 2492-2496.
Falkinham et al., "Factors influencing numbers of *Mycobacterium avium*, *Mycobacterium intracellulare*, and other mycobacteria in drinking water distribution systems", *Applied and Environmenta Microbiology*, vol. 67, No. 3, Jun. 2001, 1225-1231.
Higgins et al., "Identification of *Mycobacterium* spp. of veterinary importance using rpOB gene sequencing", *BMC Veterinary Research*, vol. 7, No. 1, Jan. 1, 2011, 1-14.
Hilborn et al., "Molecular comparison of *Mycobacterium avium* isolates from clinical and environmental sources", *Applied and Environmental Microbiology*, vol. 74, No. 15, Aug. 2008, 4966-4968.
Intl PCT/US2013/029072,International Search Report and Written Opinion mailed May 29, 2013, 1-14.
Intl PCT/US2013/029093, , "International Search Report and Written Opinion mailed", May 27, 2013, 1-13.
Johansen et al., "Distribution of IS1311 and IS1245 in *Mycobacterium avium* Subspecies Revisited", *Jounal of Clinical Microbiological*, vol. 45, No. 5, May 1, 2005, 2500-2502.
Le Dantec, et al., "Occurrence of Mycobacteria in Water Treatment Lines and in Water Distribution Systems", *Applied and Environmenta Microbiology*, vol. 68, No. 11, Nov. 2002, 5318-5325.
Pate et al., "IS1245 RFLP-based genotyping study of *Mycobacterium avium* subsp. hominissuis isolates from pigs and humans", *Comparative Immunology, Microbiology & Infectious Diseases*, vol. 31, No. 6, Nov. 1, 2008, 537-550.
Santos, et al., "Detection and identification of mycobacteria in the Lisbon water distribution system", *Water and Science Technology*, vol. 52, No. 8, 2005, 177-180.
Shin et al., "Efficient Differentiation of *Mycobacterium Avium* Complex Species and Subspecies by Use of Five-Target Multiplex PCR", *Journal of Clinical Microbiology*, vol. 48, No. 11, Nov. 2010, 4057-4062.

* cited by examiner

*Primary Examiner* — Suchira Pande

(57) ABSTRACT

Disclosed are compositions, assays, methods, diagnostic methods, kits and diagnostic kits for the specific and differential detection of a non-*Mycobacterium avium* subsp. *paratuberculosis* (non-MAP) organism, wherein a non-MAP organism is a *Mycobacterium avium* complex (MAC) organism that does not belong to the *Mycobacterium avium* subsp. *paratuberculosis* (MAP) organism, from samples including veterinary samples, clinical samples, food samples, forensic sample, an environmental sample (e.g., soil, dirt, garbage, sewage, air, or water), including food processing and manufacturing surfaces, or a biological sample. Exemplary non-MAP organisms including *M. avium* subsp. *avium* (MAA), *M. avium* subsp. *hominissuis* (MAH), and *M. avium* subsp. *silvaticum* (MAS) can be detected by the present compositions, kits and methods.

9 Claims, 6 Drawing Sheets

Gel Electrophoresis Results- Sample 10-4249 MAH

Lanes numbered 4, 5, 9 and 11 show assays with 100% sensitivity and specificity

Gel Electrophoresis Results- Sample 10-4249 MAH

Lanes numbered 4, 6, 8, and 9 show assays with 100% sensitivity and specificity

Gel Electrophoresis Results- Sample 10-4249 MAH

Lanes numbered 2, 5, 6, 8 and 11 show assays with 100% sensitivity and specificity

Gel Electrophoresis Results- Sample 10-8425 MAP

Lanes numbered 4, 5, 9, and 11 show assays with 100% sensitivity and specificity. No cross-reactivity seen with MAP.

Gel Electrophoresis Results- Sample 10-8425 MAP

Lanes numbered 4, 6, 8, and 9 show assays with 100% sensitivity and specificity. No cross-reactivity seen with MAP.

Gel Electrophoresis Results

Lanes numbered 2, 5, 6, 8, and 11 show assays with 100% sensitivity and specificity. No cross-reactivity seen with MAP.

SEQUENCE LISTING

<160> NUMBER OF SEQ ID NOS: 47

<210> SEQ ID NO 1
<211> LENGTH: 899
<212> TYPE: DNA
<213> ORGANISM: Mycobacterium avium

<400> SEQUENCE: 1
cccaagcggg ccaatcggtt taccgcggca ctcccttgcc gagtcggcgg ttggatagtg    60
tacttgtcca cgtggaggga agcagctggt gactgtccgg cgcggtttcg gtcgtgcacc   120

-continued

```
ggcgggactc tgcgttgccg cagcccttgt tctcagcggt ggcgcgtgcg caacgcataa      180
gcagcagcct gccgcggctc cagcaaccct tagggctgcg cccgatcaac tcgggccgtg      240
cgcgccggat cggttggcgc gctgcgtacc cgggctggct gacgtcgacg agaacctctt      300
cggcggcgtc gctgcgtacc agcctgatcc aggcttcgcc tcggtgccgc cctcggccgc      360
tcgggaggct gcacccgagg agtgccaaca cctgccaagg tttggcgccc aggccggtcg      420
cgaactcgat gtggagtatc agcccgcgag ggacaccaac gggaggcctt taagcaaccg      480
gttcccggcc aatggtggcg attacgttcg acttcggttc acggtcgccg gcgacggcga      540
tgatatcggg actgcgatgg cggcgtgggc cgtcgatgt ccgatgtggg ccgtggccca       600
gtcgatgaat gacagcggga tccagggctg gctcgtcgcc gagtccggcg agcacctgag      660
ccggtaccaa tcgggcgatg tcgcgtcgca gtggccctat gtctcgaaca cggcagcggt      720
agtgctaccc aacaaggtga tcgtccaggc ctggtataca accaacgacc cgtccgccgc      780
atcgcggaac cagttgctgt cgcagttgat cggggcgtct gggcatccac ggccacgctc      840
tgctctgccg cccaaactcg ccgactggag ccaagcgcag atctcgacgc tgcttcctg      899
```

<210> SEQ ID NO 2
<211> LENGTH: 1064
<212> TYPE: DNA
<213> ORGANISM: Mycobacterium avium

<400> SEQUENCE: 2

```
gtggtgcggc cctcgaaggt caccgccggc gcttgcgggc tgcgctgtgc ctgcgcggtg       60
aacagcgccg ggatcgacgt ccgggtggcg ggccggtcca ggaccgcccg ggcgccccag      120
tcgtgcagcc gctggtgttc ggccgggtcg agcacgtcga tcgacgacag cggccgtgcc      180
gggtcggcgg tcatggcgac cagtacccgc cgcatccgct cgatcagcgt cgcgatgtcc      240
tcgtcgtcga aaacccgtgt ggcgtattcg atttggaggc gcagctgcga cccgggctgg      300
gcctgcacgg tcagcgggta gtgggtggat tcgcggctgg tgatgtcggt gacgccagc      360 tcctggtcgc cggacagcgc gccggcgtcg atcgggtagt tctcgtaggc gaacagcgtg      420
tcgaaaagct tgtcctggcc ggtgattcgg tggatctcgt tgagcgccag gtgctggtgg      480
tcgagcgtgt ggttgtaggc gccttgcagc tggtgcagca ggtcgacggt gctggtggtc      540
gcggtgatgt tcgcccgcac cggcacggtg ttgatcagca ggcccaccat cgtgtcggcg      600
ccgggcacct ccgcgggccg gcccgacacc gtggtgccga agacgacgtc gcgttgcccg      660
gtgagggcgc acagcaggcg cgcgaacgcc gcctgcagca cggtgttgac ggtggtgtgg      720
caggaccggg ccaagtcggt gacggcccgg gtcaggtcgg cgggcagggt gaacgtctcg      780
acctgttgcg gcccgagctc gacggggtcc tgggcccga ccaggtcgg ggtgtcgaag       840 ccggcgaaca cctcggccca cgccgcgcgg gcggcgtcga ggtcccgttc ggccagccag      900
tcgacgaagc gcgcggtaggg cgccggcgcc ggaagccgct gaccgtagta ggcggcgaag      960
atctcgccca acaggatcgg catcgaccag ccgtccagca cgatgtggtg gttggtcagc     1020
agcagccggt gccggtcggt cgcggtgcgc accagcgcca cccg                      1064
```

<210> SEQ ID NO 3
<211> LENGTH: 350
<212> TYPE: DNA
<213> ORGANISM: Mycobacterium avium

<400> SEQUENCE: 3

```
gcccagcaat caaaacatgc atatcgggtg ccgcaccgca aaccaggctg gcgacgccga    60
acacggccag ccccagcaga tacgacgccc gcgcgccgac gcgcagcagc atcggattga   120
ccatggtggc cgcgaccacc gagccgacca gatacagcgt cgtcacccac gcgtagagcc   180
gactgccgcc gatctcggcg atggtgttgg caacaagct ggtggtcagg aactcattcg    240
tggcgtagag cgccaccccg ccggcgagca ggatcgaggt cctcagatac ctggcgccca   300
gcagctctcg ccagccgccg gtgatggtcg ccgcatccgt cacccctcta              350
```

<210> SEQ ID NO 4
<211> LENGTH: 1395
<212> TYPE: DNA
<213> ORGANISM: Mycobacterium avium

<400> SEQUENCE: 4

```
tgccagcgaa tggcactggc tccacacctg atccggtccc agggtgatgc cggtgtccag    60
cgacgcgaac agttgggtga tgttgcggtg gctgacggcc actcccttgg gttcgccggt   120
ggtgcccgag gtgtagatca cgtgggcgat gtcgccggcg gcgggcccg gccggccgg     180
ttcggtggcc gggtagtccg ccaacgccgg atcgtcgagg tcgacgatcg ccgcgccgag   240
cccggtcagc cgggagcgcg atcccgcatc ggtcaccacc accccgcagat cggcgtcggc   300
gacgatgaag gctatccgcg ccgccggcac cgccggatcc atcggcacgt acgccgcgcc   360
cgccttcagt accccaggat cgcgacgac cgcctcggcg gaacggtcca gcagcaaccc    420
cacgtactgc ccccggtcca cgccgtgctg aatcagcaag tgcgccagcc gattcgctgt   480
ctcgtcgacc tcccgatagg tccagcagcg gtccgcgctg ctgatcgcca ccgccccgg    540
cacccgctgc gcccaggcgc cgaacagcgc gggcaccgag gcgcccgtcg ttgaccggcc   600
cagcgccgcg cggttgccga atatgtcgag ccgggcaaac tcggtgtcct cgagcacctc   660
gatcgacgag aggtgccggc ccgggtcggc ggtcaggacg tcgagcaccc ggcgcagccg   720
ctcggtgagg gtgcggatgg tgtccgcgtc gaagacgtcg gtgcggaatt ccaccgttcc   780
ggcgatgccg gcgggccggc cctcctcggt ccagcgttcg cacagggaga aggtcagatc   840
cattcgagcg gtgccgatgt cgatcggcag cgccgcgacc tccagctcgc ccaggcgcag   900
ccgcgtcgga tcgtcgccgc gccaggtcaa catcacctga atcagtgggt ggtgggccag   960
cgatcgggtg gggttgagcc gctcgaccag gatttcgaag gcacgtcct ggtgttcgta   1020
ggcggccagg ctgcgttggc gcacccgggc caggatttcg ccgacggtgg gatcaccgga  1080
caaatcgacg cgcagcacca gggtgttgac gaagaacccg accaggtcat caagagccgg  1140
gtcaccacgc ccggcaatcg gaaaacccac cgccacatca caactcgcac cgagcttggc  1200
cagcagcacc gccaagccgg cctgcaccac catgaaactg gtcgcgttat gcacccgggc  1260
cagggccgat acctgctgct gcagcgacgc cggccagtcg atgtccaccc gagccccacg  1320
atgatcagcc accgccggat acggccgatc cgtcggcaac gccaaccgct cgggcaaccc  1380
ggccaacgcc tcctg                                                    1395
```

<210> SEQ ID NO 5
<211> LENGTH: 946
<212> TYPE: DNA
<213> ORGANISM: Mycobacterium avium

<400> SEQUENCE: 5
tggtttcggg cggaaggttc gccagccagt aggcctcgtc gtcgcggtag tcggccgagg 60
attcgtagtg cgactcgcac tcgaccagct cccgcagcga gccgaagacg gccgtcggga 120
tgggtccggc ggcgacgatc gcggagtaga tggaggcgat gcggtgaccg accagcccga 180
cgccggtgcc gtcgatgacg atgtggtggc agcaggcgaa caagtagaac tggtcccgcc 240
gggtcgcaaa gagggcgaac cggaacaacg gcccggacag cggcatcggc gtgcgctgga 300
tcgccagcgc ccggcggcgg gcctcggcca ccgggtcgtc caggccgctc aggtcgtcga 360
aggtcagctc gacgtccgga tgctcgatcg cccgctggta gaccgcgccg tccacctcga 420
agaacgcgac acgggcgggt tcagcctcct gcaccgcctg ccggatcgcc cagtgcaacg 480
cgtcgcgctc gacgcggccg tcgatgcgca cgaacaggcc gagctgccac tcggtgctgg 540
agtgacccgt tgcctgcgca agccagatgt ctagctgtcc gcgcgtaagc ggaagtgctt 600
gagcatcaag ctccatccat ctccccaacc acagggtctg cctttcaacc ccccggttga 660
tgaagccgct cgagcaagtg ttctctaccc ggtgcggccc cggcgcgcgg cgcgatccgc 720
tctgccgtgc tccacccggc gaccggctgg agcgccggca aagacggacc gcaaccgtgg 780
ctgccctcgt ggtggaccga ggcggcgaag ccggcggctg tcgccaccga atgcttggcg 840
ctcaccgact cccaaggcct cgtagtcaac acgagtgcaa cagttgggaa ggctagtaga 900
cgacaacccc gctggtccag agttattcaa acttaatgtc ctgtga 946

<210> SEQ ID NO 6
<211> LENGTH: 747
<212> TYPE: DNA
<213> ORGANISM: Mycobacterium avium

<400> SEQUENCE: 6
cccatactcc gggcaacggc ccaagttctc ggcatcgcca acggcgacgc cggcctgcat 60
cacaacccgc gcacgggttt ccgcgtcacc aatcagggtg agttgtacgg cgtcgcaacc 120
ttggcttagg tgtcaaaaaa cggtgaaaga aggctgcggt ggctggccat ctgacgatgc 180
agttggaggc gatggcgtcg gccgcacaca tcctgacaaa ccaagccgac ggcttcagca 240
gcgaactcga cagcatcgcc gacgactggc gcaatctgtc atcgacgtgg caaggcgccg 300
ccgcatctga tttccggccc gcatgggatg agtggcacca aggcgcaaag gccgtcgcaa 360
cgctgctatc ggaacactcc cagctgttgc tccgctcact ggacctcatg ctcgaccacg 420
agacgattgc cgcgagagcc ttcgccgccc tgtccccaac ggatccggaa tcatgagccg 480
ccgttacacg gtcgaccctg aggcactgtc gcattttgcc gaccgactgg cgaaattcac 540
tgccagcgcg gaacaaattg ccgcggccgt cgaccaatgc atcgccgaac tccacggttc 600
ctggctgggt cgcggcgcag acgccgagcg cgagtaccac caaagatggg tagcagccga 660
caaacaaatg cgagaagcgc tcaccgaatt gcgcaccaat gtggagaggg cgcaccgcaa 720
ctatgacggt gtggcccaac acaatac 747

<210> SEQ ID NO 7
<211> LENGTH: 902
<212> TYPE: DNA
<213> ORGANISM: Mycobacterium avium

<400> SEQUENCE: 7
ccacgccaga tagggcgcgt gcgcggcaac gtaccgctcg gcgctgggcc cctgccacgc 60
atcggattgc gccgccgcca gcgtcgcgct gagttccgcg gcggccgacg cataggtttc 120

```
gctcaacgac gtccaggacg cggccgcgct cagcaggccg gccggtcccg gcccgctgct      180
gagcagcgtg gaatggacct ccggggcgaa cgccatccac accggcgcgg tcatggccga      240
agactcctcg tcgggctggg tcaggaaccg ccggggctgt tcggcggcgc acgggtcagc      300
ccggtagtag tcgcaccggg gccgcgagaa gttccggcgc ggcgccgatt catggatgac      360
tcatgaaaaa ccggccgcga tcggggttcg cggccggttt gtcgctcggc gggtcaggcc      420
cgcacggcgc tcaccagggt gttgcgcgcg atcatcggcc cggcctcggt gtccgggccg      480
ggcaccggac ggccgacctg gcgcaggtag tcggccagcg gggtgggcac cgcggtccag      540
ccgcggctgc cgaaccactc ggcggccggc gcgcactgtt cgttgtagac gagctgaaag      600
aacattcgct gctcgccctg ctcgttggcg gcgcgttcgg cggccaccgc ggcctcgaag      660
tcctcgggcg tcatcgggcg ccctcctcg accgcgacgt ggctgccgtg gccggccagc      720
gcgtcgatgc cggtgaacag ctgctcctgg gcgctggccg gcagatagat cagcaggccc      780
tcggcgatcc acgccgacgg cttgtccggg tcgaatccgc tgtcccgcaa ggcctgcggc      840
cagtcctcgc gcagatccac ggcgatctca cggcgctcgg gcgcgggtg ggcgtcgacg      900 cc                                                                    902
```

<210> SEQ ID NO 8
<211> LENGTH: 1612
<212> TYPE: DNA
<213> ORGANISM: Mycobacterium avium

<400> SEQUENCE: 8

```
gggtcacccg caggatcacc gccacgctgg ccgccgcggg gccgagggcc tcgacgccgg       60
ccgacaccgt ggccgcctgc gcggtgacgt tgtgctgggc cagctcggcg ctggacttgg      120
tgtactgctc cttgaacgcc gcggcgtgtt cgggcaccac catcgccgcg gcccggtcga      180
tggcgccggt cggtgcggtc gggctgaacg aggccatcga ctcggccatg ccggtggcga      240
tcgcgacgac cttgtgggag tcgtcggtga agtcacggtc ggccctggtc cagtgcgtgt      300
agccggtcgc gacggccgcc gccagcgcgg ccgtgcacag cagcaccacc gccaaccgca      360
gccccggcgc gtcgtcgtcg gtgccgaggc tgaccgaatc gcggcgcagc agccagaaat      420
tgatcagcac gccctcgacg atcaacaaca ccagcaccga gcaggccgac acccaccaca      480
gcggccagcc gagcaccacg ccgatggcca gcagggccgc aatcgcggcc accggggccg      540
cgatgtcgaa ggcgaacaac cgccagatgt ttctcatcgc atctctcacc tgatcgagga      600
cagcccggag atcatcagct tgccgtccac gtccggagacg tccaggcgca ggctccagtg      660
cacggtctgc ggcttggcgc cgacgttttc gctcaccgag gtggcgacca gcagcaccga      720
gtcggtgcgg gtggcgaacg gcggcagctt ggtggtgacc ggcggccgcg cggcgcccgg      780
ctgggcgtcc aggtcgtggt gcacggtttc gatcgccacc gcgtccaccc gcccgctgct      840
cttggactgc agcttctcca ccaccgcccg gtagggctgc accgcggcgt cgaagtcggt      900
gttgagctcg ccgaccgtgc cgtcgtgcag ccgctgcagg ctggcgtcga cgttgccgct      960
gttcatgttg atcagcacgt tcgcccagtc cgcggcggtc cgcatgaccc ggctcaaata     1020
gctgcgctcg cgacctggt cgcggtggtc ggaccagatc agggcggcga gcaccaccgc     1080
ggccacggac agcacgccga gaaccgttga ggcgacgccg taatgggaga agattcggcc     1140
gtccgcggct tcgggcggtt cgtcggcatc ggaatcttgt tcggcaggtg gctcggttcg     1200
ctcgccgtcg gacatggccc gatcgtcgca cccggcagag atggaaggat ggcggggtga     1260
cgaatacggc catccgctcg gggatcgacc tgagccatgt cgacgacagc atccgcccgc     1320
```

```
aagacgacct gttcggtcac gtcaacggcc gctggctggc cgaatacgag atacccgccg   1380
accgggccac cgacggcgcc ttccggcagc tctacgaccg cgccgaggag caggtgcgcg   1440
acctgatcgt cgaggccagc gagcagggtg cggccgccgg cggtgacgac gcccaacgca   1500
tcggcgacct gtacgccagc ttcctggacg aggacaccgt gcagcgccgc ggcctgcagc   1560
ccctgctcga cgagctggcg ctcatcgacg aggccgccga cgccgccgcc ct           1612
```

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggatcgccc agtgcaa                                                    17

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcagctcgg cctgt                                                      15

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcgtgcgcat cgacggcc                                                   18

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggcgcaatc tgtcatcga                                                  19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgccttggtg ccactcat                                                   18

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cgccgccgca tctgatttcc                                                 20

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggctgcaccc gagga                                                      15

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcgggctgat actccacatc                                                 20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ccaaaccttg gcaggtgttg gcac                                            24

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgcggtgac gttgtg                                                     16

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttcaaggag cagtacacca agt                                             23
```

```
<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cagcgccgag ctggccca                                                      18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcgcaagcc agatgtctag                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaaggcaga ccctgtggtt                                                    20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
atgctcaagc acttccgctt acgc                                               24

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcctggtat acaaccaacg a                                                  21

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagcgtggcc gtggat                                                        16
```

```
<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tcaactgcga cagcaactgg ttcc                                            24

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agcagcatcg gattgaccat                                                 20

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgcgtgggt gacgac                                                     16

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
accaccgagc cgaccagata ca                                              22

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cccaggatcg cgacgac                                                    17

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggcgcacttg ctgattca                                                   18
```

```
<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ctgctggacc gttccgccga                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctggccggca gatagatcag                                                    20

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccttgcggg acagc                                                         15

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ccgacggctt gtccgggtcg aatc                                               24

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggtggtcagg aactcattcg t                                                  21

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gggcgccagg tatctga                                                       17
```

-continued

```
<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
tagagcgcca ccccgccgg                                                19

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggcgaaccg gaacaac                                                  17

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agcggcctgg acgac                                                    15

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ctggcgatcc agcgcacgcc                                               20

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cggcccgctg ctga                                                     14

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaggagtctt cggccatgac                                               20
```

-continued

```
<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
ttcgccccgg aggtccattc cac                                            23

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgggcagggt gaacgt                                                    16

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgttcgccgg cttcga                                                    16

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
cccaggaccc ggtcgagctc                                                20
```

COMPOSITIONS AND METHODS FOR DETECTION OF MICROORGANISMS OF THE *MYCOBACTERIUM AVIUM* COMPLEX EXCLUDING *MYCOBACTERIUM AVIUM PARATUBERCULOSIS*

CROSS-REFERENCE(S) TO RELATED APPLICATION(S)

This application claims priority under 35 U.S.C. §119(e) of U.S. Provisional Application No. 61/619,236, filed Apr. 2, 2012, the entire contents of which are incorporated herein by reference.

EFS INCORPORATION PARAGRAPH FOR SEQUENCE LISTINGS

The instant application contains a Sequence Listing which has been submitted in ASCII format via EFS-Web and is hereby incorporated by reference in its entirety. Said ASCII copy, created on Feb. 28, 2013, is named LT00648_SL.txt and is 20,328 bytes in size.

FIELD

The present teachings relate to compositions, methods and kits for detection and diagnosis of some members of the *Mycobacterium avium* complex (MAC) including *M. avium* subsp. *avium* (MAA), *M. avium* subsp. *hominissuis* (MAH), and *M. avium* subsp. *silvaticum* (MAS), while excluding detection of *Mycobacterium avium* subsp. *paratuberculosis* (MAP), in a variety of mammalian host species.

BACKGROUND

The *Mycobacterium avium* complex (MAC) consists of multiple *Mycobacterium avium* subspecies that can be found as environmental contaminants in soil and water and as infectious agents infecting animals such as pigs, cattle, sheep and birds. Organisms classified in the MAC complex include *Mycobacterium avium* subsp. *avium* (MAA), *Mycobacterium avium* subsp. *paratuberculosis* (MAP), *Mycobacterium avium* subsp. *silvaticum* (MAS), and *Mycobacterium* subsp. *hominissuis* (MAH). Symptoms of infection vary by host species and MAC organism. Of these MAC organisms, MAP is a bacterium that causes Johne's disease (chronic granulomatous enteritis of the small intestine) in livestock. Johne's disease results in decreased milk production, fetal loss, diarrhea and early death resulting in substantial economic loss to the livestock and diary industry.

The *Mycobacterium avium* subspecies classifications are complicated and inconsistent throughout the literature. Absent a systematic whole-genome sequencing effort for sequencing all *Mycobacterium avium* organisms, some *Mycobacterium avium* organisms are placed into subspecies based on what species they infect rather than on nucleic acid sequence similarity. Furthermore, mixed infections have also been described in the literature, further complicating classification and diagnosis.

Assays for the rapid, sensitive and specific detection of infectious pathogens are needed for differential identification of MAP and other *Mycobacterium avium* subspecies, which include MAA, MAH and MAS. Such assays are sought for differential and specific diagnostic identification of which microbe is infecting an animal.

SUMMARY

The present disclosure, in some embodiments, describes compositions, kits and methods of use thereof for specific and/or differential detection of some organisms of the MAC, which include MAA, MAH and MAS as well as MAC species of indeterminate subspecies, collectively referred to herein as non-MAP organisms, while excluding the detection of *Mycobacterium avium* subsp. *paratuberculosis* (MAP) organisms.

Compositions, methods and kits for detection and diagnosis of non-MAP organisms, in some embodiments, exclude detection of *Mycobacterium avium* subsp. *paratuberculosis* (MAP). Differentially detecting non-MAP microorganisms from MAP organisms in a variety of mammalian host species provides elimination of false positives and superior diagnostic tests. In some embodiments, the methods of the present disclosure can be used for one-step diagnostic methods.

In some embodiments, the present disclosure describes nucleic acid target sequences that are present in non-MAP organisms and absent in the MAP subspecies of organisms. These non-MAP organism specific/unique nucleic acid sequences comprise regions of non-MAP organism genomes including non-coding regions, coding regions, genes, alleles and variants thereof and/or portions and/or fragments and/or complements thereof of MAA, MAH, MAS, and MAC organisms of indeterminate subspecies. In some embodiments, a nucleic acid target sequence unique to a non-MAP organism comprises the sequence of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences.

In some embodiments, fragments as described in this application, comprise fragments having at least 10, at least 20, at least 25, or at least 30 contiguous nucleotides, including all values in-between at least 10 and at least 30 contiguous nucleotides (such as 11, 12, . . . 21, 27 . . . 29 etc.), of any of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8.

Sequences having 80%-99% sequence identity may include nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8 and include all values in-between 80% and 99%.

In some embodiments, the disclosure also relates to the nucleic sequences derived from SEQ ID No. 1-SEQ ID No. 8, which comprises sequences derived from these sequences but differing by mutations, insertions, deletions and/or substitutions of one or more bases but nevertheless hybridizing, under conditions of high stringency, with one of the above-mentioned sequences and/or fragments thereof.

In some embodiments, compositions comprising isolated nucleic acids having the sequence of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences are described. In some embodiments, isolated nucleic acid compositions comprise fragments having at least 10, at least 20, at least 25, or at least 30 contiguous nucleotides, including all values in-between at least 10 and at least 30 contiguous nucleotides (such as 11, 12, . . . 21, 27 . . . 29 etc.), of any of SEQ ID. NO: 1, SEQ ID. NO: 2, SEQ ID NO: 3, SEQ ID NO: 4, SEQ ID NO:5, SEQ ID NO: 6, SEQ ID NO: 7, and/or SEQ ID NO: 8. Isolated nucleic acids having sequences having 80%-99% sequence identity may include nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4, SEQ ID NO:5, SEQ ID NO: 6, SEQ ID NO: 7, and/or SEQ ID NO: 8 and include all values in-between 80% and 99% not explicitly disclosed.

Some embodiments describe oligonucleotide primers for use in a nucleic acid amplification method (such as but not limited to PCR) for the detection of target nucleic acid sequences that are unique to non-MAP organisms. Oligonucleotide primers of the present disclosure comprise a primer set comprising at least two primers, having at least one forward primer and at least one reverse primer, that are operable to hybridize to target nucleic acid sequences that are unique to non-MAP organisms including portions and/or fragments and/or complements thereof and/or sequences having at least about 90% identity, and/or sequences having at least about 80% identity thereto. Some embodiments describe primers operable to bind to and specifically hybrizide to target non-MAP nucleic acid sequences having SEQ ID NOs: 1-8. Some exemplary non-limiting primer sequences of the present disclosure comprise isolated nucleic acid sequences having the nucleotide sequence, of SEQ ID NO: 9, SEQ ID NO: 10, SEQ ID NO: 12, SEQ ID NO: 13, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, complements thereof and sequences having about 90% identity to the foregoing sequences.

In some embodiments, primer sets are described having at least 2 primer sets (or more than two primer sets), wherein each primer set has at least a forward primer and at least a reverse primer, that are operable to hybridize to target nucleic acid sequences that are unique to non-MAP organisms including portions and/or fragments and/or complements thereof and/or sequences having at least about 90% identity to, and/or sequences having at least about 80% identity thereto. In some embodiments, primer sets may be nested primers. In some embodiments, primer sets or primers may be degenerate primers.

Some embodiments describe oligonucleotide probe sequences for use in detection of target nucleic acid sequences and/or amplified target sequences that are unique to non-MAP organisms. Oligonucleotide probes of the present disclosure are operable to hybridize to target nucleic acid sequences that are unique to non-MAP organisms including portions and/or fragments and/or complements thereof and/or sequences having at least about 90% identity, and/or sequences having at least about 80% identity thereto. Some embodiments describe probes operable to bind to and specifically hybrizide to target non-MAP nucleic acid sequences having SEQ ID NOs: 1-8. Some exemplary non-limiting probe sequences of the present disclosure comprise isolated nucleic acid sequences having the nucleotide sequence, of SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47 and/or complements thereof and sequences having about 90% identity to the foregoing sequences.

In some embodiments, isolated nucleic acid sequence compositions of the disclosure, including primers and probes and other nucleic acids/polynucleotides, can further comprise one or more label, such as, but not limited to, a dye, a radio-active isotope, a chemiluminescent label, a fluorescent moiety, a bioluminescent label an enzyme, and combinations thereof.

The present disclosure, in some embodiments, describes methods (assays) utilizing molecular methods such as nucleic acid sequence specific amplification and detection that offer significant improvements in speed, sensitivity and specificity over traditional microbiological methods. Embodiments relate to design and development of molecular detection assays comprising identification of one or more target nucleic acid sequence that is present in a non-MAP organism to be detected and absent or divergent in organisms not to be detected (such as MAP or other non-*Mycobacterium avium* species). Some embodiments further relate to designing primers, including designing degenerate primers that can bind to and amplify one or more target nucleic acid sequences encoding for a non-MAP organism specific target nucleic acid and/or a complement and/or a fragment thereof, and using the designed primers to amplify and detect such target nucleic acid sequences.

In some embodiments, methods of detecting in a sample the presence of a non-MAP microorganism are disclosed. In some embodiments, methods of detecting the presence of a non-MAP strain are described.

The specification also discloses methods for detection of a non-MAP organism in a sample and methods to exclude the presence of non-MAP organism in a sample, wherein the detection of at least one nucleic acid sequence that is specific for a non-MAP organism is indicative of the presence of a non-MAP organism and the absence of detection of any nucleic acid sequence unique to a non-MAP organism is indicative of the absence of a non-MAP organism in the sample.

In some embodiments, methods of detection of a non-MAP organism comprise detection of one or more target nucleic acid sequences that are present uniquely in a non-MAP organism. In some embodiments unique non-MAP target sequences have SEQ ID NOs. 1-8, including portions and/or fragments and/or complements and/or derived sequences thereof and/or sequences having at least about 90% identity to, and/or sequences having at least about 80% identity thereto.

Accordingly, a method of the disclosure, in some embodiments, comprises detecting, in a sample, at least one (or more) nucleic acid sequence(s) having at least 10 to at least 25 contiguous nucleic acids of one (or more) of a non-MAP organism specific nucleic acid targets and/or complementary sequences thereof, wherein detection of the at least one nucleic acid sequence indicates the presence of an non-MAP organism in the sample. Non-limiting examples of non-MAP specific nucleic acids that can be detected include SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences. Methods of detection can also comprise identification steps and can further comprise steps of sample preparation. Such embodiments are described in detail in sections below.

One embodiment method for detection of a non-MAP organism from a sample comprises: detecting the presence of a non-MAP-specific target nucleic acid and/or a fragment or a complement thereof comprising: amplifying an non-MAP-specific nucleic acid and/or a fragment and/or a complement thereof by contacting nucleic acids present in the sample with at least one primer set, having one forward primer and one reverse primer that can specifically hybridize to and amplify the non-MAP-specific nucleic acid and/or a fragment and/or a complement thereof, under conditions suitable for amplification, and detecting an amplified nucleic acid, wherein detecting an amplified nucleic acid amplified by the primers confirms the presence of a non-MAP organism in the sample. In some embodiments, more than one primer pairs can be used to amplify one or more amplification products. Primers can be nested primers.

Non-limiting exemplary primer pairs comprise a primer pair such as SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; or complements thereof and sequences having about 90% identity to the foregoing sequences, wherein one of the two primers of each primer set is a forward primer and the other is a reverse primer.

Accordingly, an example embodiment method for detection of a non-MAP organism from a sample comprises: detecting the presence of a non-MAP-specific nucleic acid and/or a fragment and/or a complement thereof comprising: amplifying a non-MAP-specific nucleic acid and/or a fragment and/or a complement thereof by contacting nucleic acids present in the sample with at least one primer set, each primer set having one forward primer and one reverse primer, comprising the at least one primer set selected from: SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; wherein the contacting is performed under conditions suitable for hybridization of said primers to targets and further under conditions suitable for nucleic acid amplification reaction; and detecting an amplified nucleic acid, wherein detecting an amplified nucleic acid using said primers confirms the presence of a non-MAP organism in the sample.

In one embodiment method for detection of a non-MAP organism from a sample comprises: detecting the presence of one or more non-MAP specific nucleic acids and/or a fragment or a complement thereof comprising: contacting nucleic acids present in a sample with a multiplex of primer sets each primer set having one forward primer and one reverse primer, comprising a first primer set, a second primer set, and optionally a third (a fourth etc.) primer sets, under conditions optimal for an amplification reaction to obtain one or more amplified nucleic acids; and detecting the one or more amplified nucleic acids, wherein detecting an amplified nucleic acid using said primers confirms the presence of a non-MAP organism in the sample.

Some embodiments describe a method for detection of a non-MAP organism from a sample comprising: detecting the presence of one or more non-MAP-specific nucleic acids including detecting a first non-MAP specific nucleic acid and/or a fragment or a complement thereof comprising: a) amplifying from a sample a first non-MAP specific nucleic acid and/or a fragment or a complement thereof by contacting nucleic acids present in the sample with at least a first primer set, having one forward primer and one reverse primer, the first primer set designed to amplify the first non-MAP specific nucleic acid and/or a fragment or a complement thereof; and b) amplifying simultaneously from the same sample a second non-MAP specific nucleic acid and/or a fragment or a complement thereof by simultaneously contacting nucleic acids present in the sample with at least a second primer set, having one forward primer and one reverse primer, the second primer set designed to amplify the second non-MAP specific nucleic acid and/or a fragment or a complement thereof, wherein the contacting in steps a) and b) is performed under conditions suitable for a nucleic acid amplification reaction; and detecting at least one amplified nucleic acid amplified by either the amplification reactions of steps a) and/or b), wherein detection of at least one amplified nucleic acid indicates the presence of a non-MAP organism in the sample. In some embodiments a first and a second amplification product can be detected to indicate the presence of a non-MAP organism in the sample. Furthermore, the process can be optionally repeated to detect a third, a fourth and additional non-MAP specific nucleic acid molecules. Non-limiting examples of non-MAP specific nucleic acids that can be detected include SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences.

In some embodiments, not detecting any amplified product using one or more methods described above can be used to exclude the presence of a non-MAP organism in a sample.

Amplification reactions can comprise a PCR amplification, an end-point determination, a quantitative amplification, a real-time PCR such as a SYBR® Green Assay or a TaqMan® Assay. A real-time assay can comprise the use of a labeled probe specific to hybridize to a non-MAP target nucleic acid region in addition to hybridization with one or more primer sets.

Detection can be performed by a variety of methods, such as but not limited to, a nucleic acid amplification reaction such as described in the paragraph above. Detection in some embodiments can be performed by hybridization using probes specific to amplified nucleic acid sequences encoding a non-MAP specific target nucleic acid sequence. Combinations of amplification and hybridization can be used for detection according to some embodiments. Example probe sequences of the disclosure that can be used for detecting in a method of the present disclosure are described in SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, and/or SEQ ID NO: 47 and/or complements thereof and sequences having about 90% identity to the foregoing sequences.

In some embodiments, probes can be used to detect and/or to identify a nucleic acid sequence amplified described in the methods above. For example, a probe having SEQ ID NO: 11 can be used to detect an amplified nucleic acid amplified by using primer set having SEQ ID NO: 9 and SEQ ID NO: 10; a probe having SEQ ID NO: 14 can be used to detect an amplified nucleic acid amplified by using primer set having SEQ ID NO: 12 and SEQ ID NO: 13; a probe comprising SEQ ID NO:17 can be used to detect an amplified nucleic acid amplified by using primer set having SEQ ID NO: 15 and SEQ ID NO: 16; a probe having SEQ ID NO:20 can be used to detect an amplified nucleic acid amplified by using primer set having SEQ ID NO: 18 and SEQ ID NO: 19; a probe having SEQ ID NO: 23 can be used to detect an amplified nucleic acid amplified by using primer set having SEQ ID NO: 21 and SEQ ID NO:22; a probe having SEQ ID NO: 26 can be used to detect an amplified nucleic acid amplified by using primer set having SEQ ID NO: 24 and SEQ ID NO: 25; a probe having SEQ ID NO: 29 can be used to detect an amplified nucleic acid amplified by using primer set having SEQ ID NO: 27 and SEQ ID NO: 28; a probe having SEQ ID NO: 32 can be used to detect an amplified nucleic acid amplified by using primer set having SEQ ID NO: 30 and SEQ ID NO: 31; a probe having SEQ ID NO: 35 can be used to detect an amplified nucleic acid amplified by using primer set having SEQ ID NO: 33 and SEQ ID NO: 34; a probe having SEQ ID NO: 38 can be used to detect an amplified nucleic acid amplified by using primer set having SEQ ID NO: 36 and SEQ ID NO: 37; a probe having SEQ ID NO: 41 can be used to detect an amplified nucleic acid amplified by using primer set having SEQ ID NO: 39 and SEQ ID NO: 40; a probe having SEQ ID NO: 44 can be used to detect an amplified nucleic acid amplified by using primer set having SEQ ID NO: 42 and SEQ ID NO: 43; a probe having SEQ ID NO: 47 can be used to detect an amplified nucleic acid amplified by using primer set having SEQ ID NO: 45 and SEQ ID NO: 46.

In one embodiment, disclosed is an assay for the detection of a non-MAP organism in a sample comprising a) hybridizing a first pair (or set) of PCR primers selected from a row in the Table 3 described as forward primers and reverse primers (selected from primer sets described in the paragraph above), and complements thereof to at least a first non-MAP target polynucleotide sequence and/or fragment thereof; b) amplifying said at least first target non-MAP polynucleotide sequences; and c) detecting said at least first and said at least second amplified target polynucleotide sequence products; wherein the detection of the at least first amplified target polynucleotide sequence product and the detection of the at least second amplified target polynucleotide sequence product is indicative of the presence of a non-MAP organism in the sample. The method can also comprise hybridizing a second pair of PCR primers selected from another row in Table 3 described as forward primers and reverse primers, and complements thereof to at least a second target non-MAP polynucleotide sequence and/or fragment thereof. Optionally, the method can comprise hybridizing with a third, fourth, . . . eighth, etc. sets of PCR primers selected form Table 3 to amplify a third, fourth, . . . eighths, etc. target nucleic acid sequences.

In further embodiments, the detection can comprise using hybridization with one or more probes. Probes that can be used are described in Table 3 which describes different probes specific to different amplified non-MAP target sequences. Primer-probe combinations are outlined in the Table 3 and also set forth in the sections above (for example, amplification product amplified using primers SEQ ID NO:9 and SEQ ID NO:10 can be detected using probe SEQ ID NO:11).

In some embodiments, hybridization can comprise at least a first probe and a second probe, the first probe further comprising a first label and said second probe further comprising a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye. In some embodiments, such as real-time PCR assays, a single probe can comprise two labels.

In some embodiments, any detection method described above can further comprise preparing a sample for PCR amplification (prior to hybridizing), for example, but not limited to (1) bacterial enrichment, (2) separation of bacterial cells from the sample, (3) cell lysis, and (4) NA extraction (e.g., DNA, RNA, total DNA, genomic DNA). In some embodiments, a detection method can comprise nucleic acid/DNA isolation from a sample. In some embodiments, there is no need for cell lysis and/or nucleic acid isolation and an isolated cell or a lysed cell can be directly subject to PCR.

Samples may include without limitation, veterinary samples, animal-derived samples, clinical samples, food/beverage samples, water samples, and environmental sample. Veterinary samples may be derived from animals such as but not limited to all ruminants, cattle, sheep, bison, deer, foxes, hares, rabbits, pigs and birds such as but not limited to hens, fowl, quail, turkeys, ducks, geese, ostrich, emu, and wild birds.

Methods include multiplex assays such as polymerase chain reactions, wherein hybridizing and amplifying of a first pair of polynucleotide primers occurs in a first vessel and hybridizing and amplifying of a second pair of polynucleotide primers occurs in a second vessel, or hybridizing and amplifying of a first pair of polynucleotide primers and hybridizing and amplifying of a second pair of polynucleotide primers occurs in a single vessel, the detection is a real-time assay, the real-time assay is a SYBR® Green dye assay or a TaqMan® assay. Probes of the disclosure can be used in Taqman® type of PCR reactions in which case they can be labeled with two labels. Methods can also comprise using additional primers such as a third primer pair and a fourth primer pair and so on.

A method of the disclosure can further comprise providing a first probe and a second probe (and additional probes such as a third probe and a fourth probe and so on), wherein the first and second probes are different from each other, the first probe operable to identify a first amplified target polynucleotide sequence and the second probe operable to identify a second amplified target nucleotide sequence, the first probe further comprises a first label and the second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and the second probe is labeled with VIC® dye; and hybridizing the first and second probes to the PCR amplified fragments to detect the presence of the first amplified target polynucleotide sequence and the second amplified target polynucleotide sequence from the sample.

Some embodiments describe kits suitable for identifying the presence of a non-MAP organism. Such a kit can comprise at least one set of oligonucleotide primers for use in a PCR process for the detection of a non-MAP target nucleic acid sequence.

A first probe may further comprise a first label and a second probe further comprise a second label, both labels are selected from a dye, a radioactive isotope, a chemiluminescent label, and an enzyme, the dye comprises a fluorescein dye, a rhodamine dye, or a cyanine dye, and the first probe is labeled with FAM™ dye and said second probe is labeled with VIC® dye. Kits may without limitation contain other buffers, molecular bio reagents, and one or more container means for kit components.

In the following description, certain aspects and embodiments will become evident. It should be understood that a given embodiment need not have all aspects and features described herein. It should be understood that these aspects and embodiments are merely exemplary and explanatory and are not restrictive of the invention. It is to be understood that both the foregoing general description and the following detailed description are exemplary and explanatory only and are not restrictive of the invention, as claimed.

The accompanying figures, which are incorporated in and constitute a part of this specification, illustrate several exemplary embodiments of the disclosure and together with the description, serve to explain certain teachings. These and other features of the present teachings are set forth herein.

DESCRIPTION OF THE DRAWINGS

The skilled artisan will understand that the drawings described below are for illustration purposes only. The drawings are not intended to limit the scope of the present teachings in any way.

DETAILED DESCRIPTION

Figure 1:
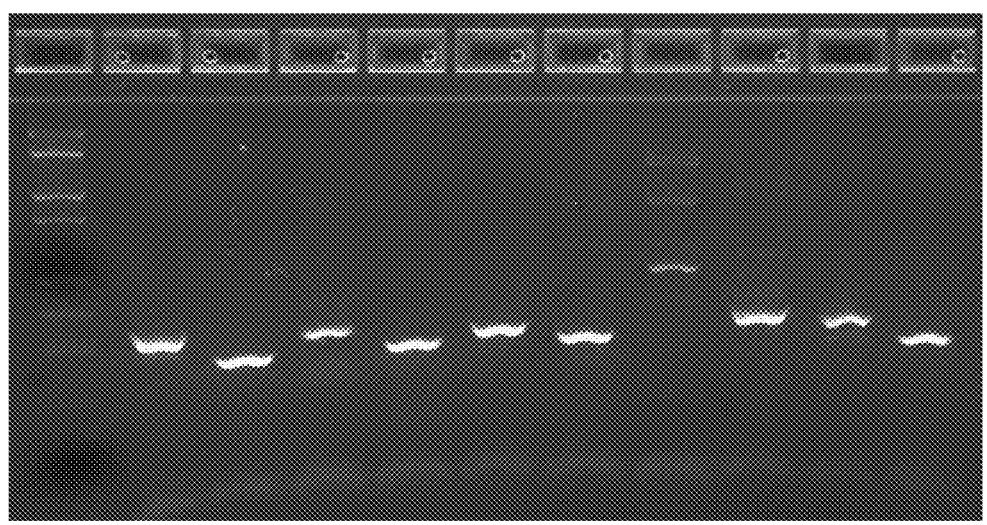
FIG. 1 illustrates a gel electrophoresis profile, according to one embodiment of the disclosure.

The present disclosure, in some embodiments, describes compositions, kits and methods for detection and diagnosis of microorganisms of the MAC that are not MAP, which include MAA, MAH and MAS as well as MAC species of indeterminate subspecies, collectively referred to herein as non-MAP organisms and excluding the detection of *Mycobacterium avium* subsp. *paratuberculosis* (MAP) organisms. Accordingly described here are compositions, kits and methods for detection and diagnosis of non-MAP organisms are described herein. Some embodiments describe specific detection of non-MAP from a sample even when MAP organisms are present in the same sample. Diagnosis and diagnostic methods of the disclosure can include detecting the presence of a non-MAP organism to diagnose a non-MAP organism induced disease or condition. Any animal or human disease or condition caused by a non-MAP organism is contemplated to be diagnosable by the detection methods disclosed herein that can detect the presence of a non-MAP organism as defined herein.

The classification of *Mycobacterium avium* subspecies has been unorganized absent a systematic whole-genome sequencing effort for sequencing different species of these organisms. Some organisms have been traditionally placed into subspecies based on what species they infect rather than on nucleic acid sequence similarity.

The *Mycobacterium avium* complex (MAC) consists of multiple *Mycobacterium avium* subspecies that can be found as environmental contaminants in soil and water (Covert et al., 1999; Falkinham et al., 2001; Le Dantec et al., 2002; Santos et al., 2005; Hilborn et al., 2008), as well as infectious agents for animals such as pigs, cattle, sheep and birds (C. Cayrou et al 2010). Organisms classified in the MAC complex include *Mycobacterium avium* subsp. *avium* (MAA), *Mycobacterium avium* subsp *paratuberculosis* (MAP), *Mycobacterium avium* subsp *silvaticum* (MAS), and *Mycobacterium* subsp *hominissuis* (MAH). Symptoms of infection vary by host species and MAC organism (C. Cayrou et al 2010).

MAP is a bacterium that infects livestock and several herd animals and causes Johne's Disease which is characterized by chronic granulomatous enteritis of the small intestine. In livestock especially diary animals such as cows, sheep and bison, Johne's disease results in decreased milk production, fetal loss, diarrhea and early death resulting in substantial economic loss to the livestock industry. MAP is also believed to be linked to human Crohn's disease.

Common methods used for identifying MAC subspecies include DNA sequencing, particularly of the 16S and rpoB genes, and RFLP (restriction fragment length polymorphism) analysis (C. Cayrou et al 2010). In some cases, presence of nucleic acid insertion sequences has been used to detect these organisms.

The present disclosure describes assays that can distinguish and detect non-MAP organisms from MAP organisms. Next-generation sequencing, using an Ion Personal Genome Machine (Ion PGM) was performed to obtain complete genome sequences for 16 *Mycobacterium avium* subspecies. The 16 *Mycobacterium avium* subspecies that were sequences included: one *M. avium silvaticum* sample; four *M. avium avium* samples; two *M. avium hominissuis* samples; three *M. avium* samples with an unknown subtype (indeterminate subspecies); and six *M. avium paratuberculosis* samples. The sequenced genomes were analyzed for the presence of all previously known insertion sequences as well as to determine new target sequences. A partial ISMAP02 sequence was found in all organisms indicating that ISMAP02 is not an optimal sequence to use for a non-MAP or a MAP-specific assay. Other insertion sequences, including IS901 were also found to be non-specific for MAP. The IS901 sequence was present in the *M. avium* subsp. *silvaticum* sequence, and two of the *M. avium* subsp. *avium* sequences (strain numbers 11-4751 and 10-9275).

In one embodiment of the current teachings, bioinformatic and direct DNA sequencing comparisons of several *Mycobacterium avium* species were conducted to identify non-MAP-specific target nucleic acids sequences. Alignment of these sequences using custom algorithms identified several non-MAP specific target regions to which primer pairs and probes of the disclosure were designed for each identified non-MAP specific target region to specifically amplify only the unique non-MAP specific target sequences against both inclusion (organism to be detected, i.e., non-MAP organisms) and exclusion genomes (organisms not to be detected, MAP organisms). The non-MAP primers and probes of the disclosure provide surprisingly unexpected results for detection of non-MAP organisms. In some embodiments, detection of non-MAP organisms is free of false positives from MAP organisms.

Exemplary embodiments of nucleic acid target sequence unique to non-MAP identified herein include nucleic acids having SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences (See Table 5 and sequence listings). Genome coordinates for SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8 are described in Table 1 below in relation to the non-MAP genome described later in the specification in Sequence Listings as *Mycobacterium avium* 104, complete genome (GenBank accession number NC_008595.1). For example, nucleic acid target sequence unique to non-MAP organisms comprising the sequence of SEQ ID. NO: 1 corresponds to a nucleic acid starting from the 317980 base pair as the left genome coordinate and the 318878 as the right genome coordinate of the non-MAP genome described as *Mycobacterium avium* 104 in GenBank accession number NC_008595.1. SEQ. ID NO: 1-8 are described here and in the Sequence Listing below.

GenBank accession number NC_008595.1 is as submitted 19 Oct. 2006 to The Institute for Genomic Research, 9712, Medical Center Dr, Rockville, Md. 20850, USA, by Fleischmann, R. D., Dodson, R. J., Haft, D. H., Merkel, J. S., Nelson, W. C. and Fraser, C. M. This is also available at http://www.ncbi.nlm.nih.gov/nuccore/NC_008595.

TABLE 1

MAA genome coordinates for
*Mycobacterium avium* 104
(NC_008595)

| Assay ID numbers | Signature left | Signature right | Signature length | SEQ ID. NO: |
|---|---|---|---|---|
| 62328, 62333, 62345, 62346, 62351 | 317980 | 318878 | 899 | SEQ ID. NO: 1 |
| 62331, 62336, 62353 | 3103764 | 3104827 | 1064 | SEQ ID. NO: 2 |
| 62326, 62330, 62339 | 3228794 | 3229143 | 350 | SEQ ID. NO: 3 |
| 62335, 62337, 62343 | 3356824 | 3358218 | 1395 | SEQ ID. NO: 4 |
| 62324, 62340, 62344, 62350 | 3363825 | 3364770 | 946 | SEQ ID. NO: 5 |
| 62323, 62325, 62334 | 4964124 | 4964870 | 747 | SEQ ID. NO: 6 |
| 62327, 62338, 62347 | 5006217 | 5007118 | 902 | SEQ ID. NO: 7 |
| 62332, 62342, 62348, 62352 | 5122685 | 5124296 | 1612 | SEQ ID. NO: 8 |

In some embodiments, compositions of the disclosure comprise isolated nucleic acids having SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences. Sequences having 80%-99% sequence identity may include isolated nucleic acid sequences that have 80%, 85%, 90%, 91%, 92%, 93%, 94%, 95%, 96%, 97%, 98% and 99% sequence identity to any one of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, and/or fragments thereof and/or complementary sequences thereof and include all values in-between 80% and 99% not explicitly disclosed. Fragments include oligonucleotides or polynucleotides having at least 10 contiguous nucleotide sequences, or at least 20 contiguous nucleotide sequences, or at least 25 contiguous nucleotide sequences, or at least 30 contiguous nucleotide sequences in any part of SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, and/or fragments thereof and/or complementary sequences thereof and sequences having at least 90% identity to the foregoing sequences.

Compositions of the disclosure comprise probe and/or primer sequences that are specific to and hybridize to (and amplify in the case of primers or detect in the case of probes) one or more target nucleic acid sequences that are unique to a non-MAP organism. A target nucleic acid sequence unique to a non-MAP organism can include a gene, a non-coding region, an allele or a complement thereof that is present in a non-MAP organism but absent from a MAP organism. In some embodiments, a target nucleic acid sequence unique to a non-MAP organism is absent from other *Mycobacterium avium* species which may otherwise be very similar or closely related. Target nucleic acid sequences as described in this disclosure can comprise portions and/or fragments and/or complements thereof and/or sequences having at least about 90% identity to, and/or sequences having at least about 80% identity thereto and/or from about 70% to about 90% identity to a target nucleic acid sequence unique to a non-MAP organism that may include a gene, a non-coding region, an allele or a complement thereof that is present in a non-MAP organism but absent from a MAP organism. Some example probe and primer sequences are described in Table 2 in sections ahead. The presently designed PCR primers and probes for use in assays by real-time PCR detected unambiguously, specifically and with great sensitivity non-MAP organisms.

Several programs for designing primers such as Primer3 (Steve Rozen and Helen J. Skaletsky (2000) "Primer3" on the World Wide Web for general users and for biologist programmers as published in: Krawetz S, Misener S (eds) Bioinformatics Methods and Protocols: Methods in Molecular Biology. Humana Press, Totowa, N.J., pp 365-386), Primer Express® software (Applied Biosystems), and OLIGO 7 (Wojciech Rychlik (2007). "OLIGO 7 Primer Analysis Software". *Methods Mol. Biol.* 402: 35-60) and variations thereof can be used for primer designing. Customized algorithms were used in the identification of unique target sequences of the present disclosure and for primer design.

In some embodiments, exemplary non-limiting compositions comprising primer sequences of the present disclosure comprise isolated nucleic acid sequences having the nucleotide sequence, of SEQ ID NO: 9, SEQ ID NO: 10, SEQ ID NO: 12, SEQ ID NO: 13, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, complements thereof and sequences having about 90% identity to the foregoing sequences.

In some embodiments, primer sets are described having at least 2 primer sets, wherein each primer set has at least a forward primer and at least a reverse primer, that are operable to hybridize to target nucleic acid sequences that are unique to non-MAP organisms including portions and/or fragments and/or complements thereof and/or sequences having at least about 90% identity to, and/or sequences having at least about 80% identity thereto. In some embodiments, primer sets are nested primers. In some embodiments, primer sets or primers are degenerate primers. In some embodiments the present disclosure describes designing multiplex primers that are suitable for multiplex PCR type of assays. Designing these primers also comprises experimentally arriving at conditions for multiplex or singleplex PCR amplification using these primers.

Some embodiments describe oligonucleotide probe sequences for use in detection of target nucleic acid sequences and/or amplified target sequences that are unique to non-MAP organisms. Oligonucleotide probes of the present disclosure are operable to specifically hybridize to target nucleic acid sequences that are unique to non-MAP including portions and/or fragments and/or complements thereof and/or sequences having at least about 90% identity, and/or sequences having at least about 80% identity thereto. Some exemplary non-limiting probe sequences of the present disclosure comprise isolated nucleic acid sequences having the nucleotide sequence, of SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, complements thereof and sequences having about 90% identity to the foregoing sequences.

Isolated nucleic acid sequence compositions of the disclosure, including primers and probes according to the disclosure, further comprise one or more label, such as, but not limited to, a dye, a radioactive isotope, a chemiluminescent label, a fluorescent moiety, a bioluminescent label an enzyme, and combinations thereof.

The specification also discloses methods for detection and/or diagnosis of a non-MAP organism from a sample, wherein the detection of at least one unique or target nucleic acid sequence that is expressed in a non-MAP organism is indicative of the presence of a non-MAP organism and the absence of detection of any nucleic acid sequence unique to a non-MAP organism is indicative of the absence of a non-MAP organism in the sample. Accordingly, some methods of the disclosure exclude the presence of a non-MAP organism in a sample absent of detection of any nucleic acid sequence unique to non-MAP organism in the sample. In some embodiments, methods of detecting in a sample the presence of a non-MAP microorganism in the presence of other *Mycobacterium avium* organisms of different subspecies, subtypes and strains, such as MAP, are disclosed.

A method of detection and/or diagnosis of a non-MAP organism comprises detection of one or more target nucleic acid sequences that are unique to non-MAP organisms including portions and/or fragments and/or complements thereof and/or sequences having at least about 90% identity to, and/or sequences having at least about 80% identity thereto. Accordingly, a method of the disclosure, in some embodiments, can comprise detecting, in a sample, at least one (or more) nucleic acid sequence(s) having at least 10 to at least 25 contiguous nucleic acids of one (or more) non-MAP specific nucleic acid targets and/or complementary sequences thereof, wherein detection of at least one nucleic acid sequence indicates the presence of an non-MAP organism in the sample. Non-limiting examples of non-MAP specific nucleic acids that can be detected include SEQ ID. NO: 1, SEQ ID. NO: 2, SEQ ID NO: 3, SEQ ID NO: 4, SEQ ID NO: 5, SEQ ID NO: 6, SEQ ID NO: 7, and/or SEQ ID NO: 8, fragments thereof, complementary sequences thereof as well as sequences having from about 80% to about 99% sequence identity to one of these sequences.

Methods of detection and/or diagnosis of a non-MAP organism of the MAC complex in a sample can also comprise identification steps and/or can further comprise steps of sample preparation. Preparing a sample for PCR amplification (prior to hybridizing with primers), can comprise steps such as, but not limited to (1) bacterial enrichment, (2) separation of bacterial cells from the sample, (3) cell lysis, and (4) NA extraction. Steps can comprise isolation of sample DNA. Some embodiments can comprise PCR without cell lysis and/or NA extraction.

Detection of non-MAP organisms by the use of methods described herein, in some embodiments, is by an amplification reaction such as a polymerase chain reaction for rapid detection. In general methods of the disclosure include comparing for presence of a non-MAP organism using suitable controls, for example, an internal positive control can be used in a PCR reaction which will have a detectable signal/positive result, a suitable negative control that will have no detectable signal. Amplification reactions can comprise one or more of the following: a PCR amplification, an end-point determination, a quantitative amplification, a real-time PCR such as a SYBR® Green Assay and/or a TaqMan® Assay.

Methods can also comprise detecting the at least one amplified nucleic acid by hybridization, mass spectrometry, nanostring, microfluidics, chemiluminescence, enzyme technologies and combinations thereof.

In one embodiment, a method for detection of a non-MAP organism from a sample can comprise: detecting the presence of an non-MAP-specific target nucleic acid and/or a fragment or a complement thereof comprising: amplifying an non-MAP-specific nucleic acid and/or a fragment and/or a complement thereof by contacting nucleic acids present in the sample with at least one primer set, having one forward primer and one reverse primer that can hybridize to and amplify the non-MAP-specific nucleic acid and/or a fragment and/or a complement thereof, under conditions suitable for amplification, and detecting an amplified nucleic acid, wherein detecting an amplified nucleic acid amplified by the primers confirms the presence of a non-MAP organism in a sample.

In some embodiments, more than one primers can be used to amplify one or more amplification products. Non-limiting exemplary primer pairs can comprise a primer pair such as SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; complements thereof and sequences having about 90% identity to the foregoing sequences, wherein one of the two primers of each primer set is a forward primer and the other is a reverse primer.

One example embodiment method for detection and/or diagnosis of a non-MAP organism from a sample comprises: detecting the presence of a non-MAP-specific nucleic acid and/or a fragment and/or a complement thereof comprising: amplifying an non-MAP-specific nucleic acid and/or a fragment and/or a complement thereof contacting nucleic acids present in the sample with at least one primer set, each primer set having one forward primer and one reverse primer, comprising the at least one primer set selected from: SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22, or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; wherein the contacting is performed under conditions suitable for an nucleic acid amplification reaction; and detecting an amplified nucleic acid, wherein detecting an amplified nucleic acid using said primers confirms the presence of a MAP organism in a sample.

In one embodiment method for detection of a non-MAP organism from a sample (and/or diagnosis of a disease/condition caused by a non-MAP organism by detecting the non-MAP organism in a sample such as a clinical/veterinary sample) comprises: detecting the presence of one or more non-MAP specific nucleic acids and/or a fragment or a complement thereof comprising: contacting nucleic acids present in a sample with a multiplex of primer sets each primer set having one forward primer and one reverse primer, comprising a first primer set, a second primer set, and optionally a third (a fourth etc.) primer sets, under conditions optimal for an amplification reaction to obtain one or more amplified nucleic acids; and detecting the one or more amplified nucleic acids, wherein detecting an amplified nucleic acid using said primers confirms the presence of a non-MAP organism in the sample.

Some embodiments describe a method for detection and/or diagnosis of a non-MAP organism from a sample comprising: detecting the presence of one or more non-MAP-specific nucleic acids including detecting a first non-MAP specific nucleic acid and/or a fragment or a complement thereof comprising: a) amplifying from a sample a first non-MAP specific nucleic acid and/or a fragment or a complement thereof by contacting nucleic acids present in the sample with at least a first primer set, having one forward primer and one reverse primer, the first primer set designed to amplify the first non-MAP specific nucleic acid and/or a fragment or a complement thereof; and b) amplifying simultaneously from the same sample a second non-MAP specific nucleic acid and/or a fragment or a complement thereof by simultaneously contacting nucleic acids present in the sample with at least a second primer set, having one forward primer and one reverse primer, the second primer set designed to amplify the second non-MAP specific nucleic acid and/or a fragment or a complement thereof, wherein the contacting in steps a) and b) is performed under conditions suitable for a nucleic acid amplification reaction; and c) detecting at least one amplified nucleic acid amplified by either the amplification reactions of steps a) and/or b), wherein detection of at least one amplified nucleic acid indicates the presence of a non-MAP organism in the sample. In some embodiments a first and a second amplification product can be detected to indicate the presence of a non-MAP organism in the sample. Furthermore, the process can be optionally repeated to detect a third, a fourth and additional non-MAP specific nucleic acid molecules.

In other embodiments, not detecting any amplified product using one or more methods described above is used to exclude the presence of a non-MAP organism in a sample.

Methods of the disclosure can also use other detection methods in addition to nucleic acid amplification reactions described in the paragraphs above. Detection in some embodiments can be performed by hybridization using probes specific to non-MAP specific target nucleic acid sequence. Accordingly, probes specific to detect one or more target non-MAP nucleic acids can be used in a sample, under conditions to promote sequence specific hybridization, to detect presence of a non-MAP nucleic acid in the sample. In some embodiments, hybridization comprises at least a first probe and a second probe, the first probe further comprising a first label and the second probe further comprising a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye.

In some embodiments, combinations of amplification and hybridization can be used for detection and amplified nucleic acid sequences encoding a non-MAP specific target nucleic acid sequence can be detected as non-MAP-specific amplification products using non-MAP specific probes. Some non-limiting example probe sequences of the disclosure that can be used for detecting in a method of the present disclosure are described in SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, complements thereof and sequences having about 90% identity to the foregoing sequences.

In one embodiment, a method for the detection of a non-MAP organism in a sample comprises: a) hybridizing a first pair (or set) of PCR primers selected from a row in the Table 2 described as forward primers and reverse primers (selected from primer sets described in the paragraph above), and complements thereof to at least a first non-MAP target polynucleotide sequence and/or fragment thereof; b) amplifying the at least first target non-MAP polynucleotide sequences; and c) detecting the at least first and the at least second amplified target polynucleotide sequence products; wherein the detection of the at least first amplified target polynucleotide sequence product and the detection of the at least second amplified target polynucleotide sequence product is indicative of the presence of a non-MAP organism in the sample. The method can also comprise hybridizing a second pair of PCR primers selected from another row in Table 2 described as forward primers and reverse primers, and complements thereof to at least a second target non-MAP polynucleotide sequence and/or fragment thereof.

In further embodiments, the detection can comprise using hybridization with one or more probes. Some example probes that can be used are described in Table 2 and different probes specific to different amplified non-MAP target sequences are described. Primer-probe combinations are outlined in the Table 2. For example, in some non-limiting embodiments, probes used to detect and/or to identify a nucleic acid sequence amplified as described methods above may comprise using the following primer/probe combinations: a probe having SEQ ID NO:11 can be used to detect an amplified nucleic acid amplified by using primer set having SEQ ID NO: 9 and SEQ ID NO: 10; a probe having SEQ ID NO: 14 can be used to detect an amplified nucleic acid amplified by using primer set having SEQ ID NO: 12 and SEQ ID NO: 13; a probe comprising SEQ ID NO:17 can be used to detect an amplified nucleic acid amplified by using primer set having SEQ ID NO: 15 and SEQ ID NO: 16; a probe having SEQ ID NO:20 can be used to detect an amplified nucleic acid amplified by using primer set having SEQ ID NO: 18 and SEQ ID NO: 19; a probe having SEQ ID NO: 23 can be used to detect an amplified nucleic acid amplified by using primer set having SEQ ID NO: 21 and SEQ ID NO:22; a probe having SEQ ID NO: 26 can be used to detect an amplified nucleic acid amplified by using primer set having SEQ ID NO: 24 and SEQ ID NO: 25; a probe having SEQ ID NO: 29 can be used to detect an amplified nucleic acid amplified by using primer set having SEQ ID NO: 27 and SEQ ID NO: 28; a probe having SEQ ID NO: 32 can be used to detect an amplified nucleic acid amplified by using primer set having SEQ ID NO: 30 and SEQ ID NO: 31; a probe having SEQ ID NO: 35 can be used to detect an amplified nucleic acid amplified by using primer set having SEQ ID NO: 33 and SEQ ID NO: 34; a probe having SEQ ID NO: 38 can be used to detect an amplified nucleic acid amplified by using primer set having SEQ ID NO: 36 and SEQ ID NO: 37; a probe having SEQ ID NO: 41 can be used to detect an amplified nucleic acid amplified by using primer set having SEQ ID NO: 39 and SEQ ID NO: 40; a probe having SEQ ID NO: 44 can be used to detect an amplified nucleic acid amplified by using primer set having SEQ ID NO: 42 and SEQ ID NO: 43; a probe having SEQ ID NO: 47 can be used to detect an amplified nucleic acid amplified by using primer set having SEQ ID NO: 45 and SEQ ID NO: 46.

In some embodiments of the present methods, one assay alone may not be definitive for detecting a non-MAP organism due to genomic similarity between the genomic regions of other non-MAP organisms. Yet, when two (or more) assays such as but not limited to the assays shown in Table 3 are used either in parallel or as a multiplex assay, e.g., in a real-time TaqMan® assay, for example, where each probe in each of the two (or more) assays has a different label for distinguishing results on a real-time PCR instrument, e.g., a 7500 Fast Real-Time PCR System (Applied Biosystems), a positive result from such an assay is indicative of the presence of a non-MAP organism. Such dual or multiplex (more than 2 assay sets) assay approach can be used to detect a non-MAP organism and also to distinguish non-MAP organism from MAP organisms. Some embodiments describe detecting at least two (or more) of non-MAP-specific target nucleic acid target regions as positive identification of a non-MAP organism.

Methods can include multiplex assays such as polymerase chain reactions, wherein hybridizing and amplifying of the first pair of polynucleotide primers occurs in a first vessel and the hybridizing and amplifying of the second pair of polynucleotide primers occurs in a second vessel, or hybridizing and amplifying of the first pair of polynucleotide primers and the hybridizing and amplifying of the second pair of polynucleotide primers occurs in a single vessel, the detection is a real-time assay, the real-time assay is a SYBR® Green dye assay or a TaqMan® assay. Methods may also comprise using additional primers such as a third primer pair and a fourth primer pair and so on.

A method of the disclosure can further comprise providing a first probe and a second probe (and optionally additional probes such as a third probe and a fourth probe and so on), wherein the first and second probes are different from each other, the first probe operable to identify the first amplified target polynucleotide sequence and the second probe operable to identify the second amplified target nucleotide sequence, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye; and hybridizing the first and second probes to the PCR amplified fragments to detect the presence of the first amplified target polynucleotide sequence and the second amplified target polynucleotide sequence from the sample.

Compositions and methods of the present disclosure are ideally suited for the preparation of a kit suitable for identifying the presence of a non-MAP organism, such as in a diagnostic kit. Such a kit can comprise at least one set of oligonucleotide primers for use in a PCR process for the amplification and detection of a non-MAP-specific target nucleic acid sequence. Some kits of the disclosure can comprise at least two sets of oligonucleotide primers for simultaneous use in a multiplex PCR process for the amplification and detection of non-MAP-specific target nucleic acid sequences. Kits can additionally comprise one or more reagents such as but are not limited to, buffers, nucleotide triphosphates, DNA polymerases, intercalating dye, primers, probes, salt, and instructions for the use of the kit.

In some embodiments, kit primers may be labeled. A kit comprising multiple pairs of primers can have primer pairs each labeled with different labels that can be each detectable separately. Probes comprised in kits of the disclosure may be labeled. If a kit comprises multiple probes each probe can be labeled with a different label to allow detection of different products that are target of each different probe.

An example kit for the detection and/or diagnosis of a non-MAP organism can comprise: at least one pair of forward and reverse PCR primers having primer pairs selected from primer pairs described in Table 2 (i.e., at least one primer set selected from: a first primer set having SEQ ID NO: 9 and SEQ ID NO: 10; and/or a second primer set having SEQ ID NO: 12 and SEQ ID NO:13; and/or a third primer set having SEQ ID NO: 15 and SEQ ID NO: 16; and/or a fourth primer set having SEQ ID NO: 18 and SEQ ID NO: 19; and/or a fifth primer set having SEQ ID NO: 21 and SEQ ID NO: 22, and/or a sixth primer set having SEQ ID NO: 24 and SEQ ID NO: 25; and/or a seventh primer set having SEQ ID NO: 27 and SEQ ID NO: 28; and/or a eighth primer set having SEQ ID NO: 30 and SEQ ID NO: 31; and/or a ninth primer set having SEQ ID NO: 33 and SEQ ID NO: 34; and/or a tenth primer set having SEQ ID NO: 36 and SEQ ID NO: 37; and/or a eleventh primer set having SEQ ID NO: 39 and SEQ ID NO: 40; and/or a twelfth primer set having SEQ ID NO: 42 and SEQ ID NO: 43; and/or a thirteenth primer set having SEQ ID NO: 45 and SEQ ID NO: 46; or sequences comprising at least 90% nucleic acid sequence identity thereof, or labeled derivatives thereof). In some embodiments, a kit can also have at least one probe selected from probes described Table 2 (i.e., probe sequences of the disclosure having SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, and/or complements thereof and sequences having about 90% identity to the foregoing sequences, each probe corresponding to the first primer set, second primer set, the third primer set, etc. as described above, respectively, selected based on which primer set is selected). Probes of the disclosure can also be useful in Taqman® type of PCR reactions in which case they can be labeled with two labels.

Another example kit for the detection and/or diagnosis of a non-MAP organism can comprise: at least two pairs of forward and reverse PCR primers (two primer pairs) selected from primer pairs described in Table 2; and optionally at least two probes selected from probes described Table 2.

A kit of the disclosure can further comprise one or more components such as but not limited to: at least one enzyme, dNTPs, at least one buffer, at least one salt, at least one control nucleic acid sample, loading solution for preparation of the amplified material for electrophoresis, genomic DNA as a template control, a size marker to insure that materials migrate as anticipated in a separation medium, and an instruction protocol and manual to educate a user and limit error in use. Components of kits can be individually and/or in various combinations comprised in one or a plurality of suitable container means.

It is within the scope of these teachings to provide test kits for use in manual applications or test kits for use with automated sample preparation, reaction set-up, detectors or analyzers. In some embodiments, an amplification product produced using a kit may be further analyzed by methods such as but not limited to electrophoresis, hybridization, mass spectrometry, nanostring, microfluidics, chemiluminescence and/or enzyme technologies.

For the purposes of interpreting of this specification, the following definitions may apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the phrase "nucleic acid," "oligonucleotide", and polynucleotide(s)" are interchangeable and not intended to be limiting.

As used herein, the phrase "stringent hybridization conditions" refers to hybridization conditions which can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically "substantially complementary" to a second polynucleotide if hybridization occurs between the polynucleotide and the second polynucleotide. As used herein, "specific hybridization" refers to hybridization between two polynucleotides under stringent hybridization conditions.

As used herein, the term "polynucleotide" refers to a polymeric form of nucleotides of any length, either ribonucleotides, deoxynucleotides, or peptide nucleic acids (PNA), and includes both double- and single-stranded RNA, DNA, and PNA. A polynucleotide may include nucleotide sequences having different functions, including, for instance, coding regions, and non-coding regions such as regulatory regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "oligonucleotide" refers to a polynucleotide of the present invention, typically a primer and/or a probe.

As used herein a "target-specific polynucleotide" refers to a polynucleotide having a target-binding segment that is perfectly or substantially complementary to a target sequence, such that the polynucleotide binds specifically to an intended target without significant binding to non-target sequences under sufficiently stringent hybridization conditions. The target-specific polynucleotide can be e.g., a primer or probe and the subject of hybridization with its complementary target sequence.

The term "target sequence", "target signature sequence" "target nucleic acid", "target" or "target polynucleotide sequence" refers to a nucleic acid present in a non-MAP organism that is not present in a MAP organism and is unique to non-MAP organisms. The target sequence can be a polynucleotide sequence that is the subject of hybridization with a complementary polynucleotide, e.g. a primer or probe. The target sequence can be composed of DNA, RNA, an analog thereof, and including combinations thereof. The target sequence may be known or not known, in terms of its actual sequence and its amplification can be desired. The target sequence may or may not be of biological significance. Typically, though not always, it is the significance of the target sequence which is being studied in a particular experiment. As non-limiting examples, target sequences may include regions of genomic DNA, regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc.

As used herein an "amplified target polynucleotide sequence product" refers to the resulting amplicon from an amplification reaction such as a polymerase chain reaction. The resulting amplicon product arises from hybridization of complementary primers to a target polynucleotide sequence under suitable hybridization conditions and the repeating in a cyclic manner the polymerase chain reaction as catalyzed by DNA polymerase for DNA amplification or RNA polymerase for RNA amplification.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art.

As used herein, "amplifying" and "amplification" refers to a broad range of techniques for increasing polynucleotide sequences, either linearly or exponentially. Exemplary amplification techniques include, but are not limited to, PCR or any other method employing a primer extension step. Other non-limiting examples of amplification include, but are not limited to, ligase detection reaction (LDR) and ligase chain reaction (LCR). Amplification methods may comprise thermal-cycling or may be performed isothermally. In various embodiments, the term "amplification product" includes products from any number of cycles of amplification reactions.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labeling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in Nonisotopic DNA Probe Techniques (1992), Academic Press, San Diego, pp. 3-28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' non-isotopic labeling of PCR probes and primers" (1995) in PCR 2: A Practical Approach, Oxford University Press, Oxford, pp. 39-54).

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "end-point analysis" refers to a method where data collection occurs only when a reaction is substantially complete.

The term "real-time analysis" refers to periodic monitoring during PCR. Certain systems such as the ABI 7700 Sequence Detection System (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "quenching" refers to a decrease in fluorescence of a first moiety (reporter dye) caused by a second moiety (quencher) regardless of the mechanism.

A "primer," as used herein, is an oligonucleotide that is complementary to a portion of target polynucleotide and, after hybridization to the target polynucleotide, may serve as a starting-point for an amplification reaction and the synthesis of an amplification product. Primers include, but are not limited to, spanning primers. A "primer pair" refers to two primers that can be used together for an amplification reaction. A "PCR primer" refers to a primer in a set of at least two primers that are capable of exponentially amplifying a target nucleic acid sequence in the polymerase chain reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The terms "complement" and "complementary" as used herein, refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

A "label" refers to a moiety attached (covalently or non-covalently), or capable of being attached, to an oligonucleotide, which provides or is capable of providing information about the oligonucleotide (e.g., descriptive or identifying information about the oligonucleotide) or another polynucleotide with which the labeled oligonucleotide interacts (e.g., hybridizes). Labels can be used to provide a detectable (and optionally quantifiable) signal. Labels can also be used to attach an oligonucleotide to a surface.

A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength.

The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a flourophore (a fluorescent quencher). This phenomenon is generally known as fluorescent resonance energy transfer (FRET). Alternatively, a quencher can dissipate the energy absorbed from a fluorophore as heat (a non-fluorescent quencher).

As used herein the term "sample" refers to a starting material suspected of harboring a particular microorganism or group of microorganisms. A "contaminated sample" refers to a sample harboring a pathogenic microbe thereby comprising nucleic acid material from the pathogenic microbe. Examples of samples include, but are not limited to, veterinary samples (samples obtained from animals suspected of harboring or being infected by a microorganism—these may include any body fluid or tissue sample), food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), milk (from animals), water samples, environmental samples (e.g., soil samples, dirt samples, garbage samples, sewage samples, industrial effluent samples, air samples, or water samples from a variety of water bodies such as lakes, rivers, ponds etc., samples obtained from animal pens/barns/farms), air samples (from the environment or from a room or a building), forensic samples, agricultural samples, pharmaceutical samples, biopharmaceutical samples, samples from food processing and manufacturing surfaces, and/or biological samples. A biological sample may include tissue samples, cell samples, blood, serum, plasma, pus, cerebrospinal fluid, bone marrow, urine, feces, saliva, mucus, milk or other materials from a human or an animal. A biological sample can be, for instance, in the form of a single cell, plurality of cells, in the form of a tissue, or in the form of a fluid.

A sample may be tested directly, or may be prepared or processed in some manner prior to testing. For example, a sample can be processed to enrich any contaminating microbe and can be further processed to separate and/or lyse microbial cells contained therein. Lysed microbial cells from a sample can be additionally processed or prepares to separate, isolate and/or extract genetic material from the microbe for analysis to detect and/or identify the contaminating microbe. Analysis of a sample may include one or more molecular methods. For example, according to some exemplary embodiments of the present disclosure, a sample may be subject to nucleic acid amplification (for example by PCR) using appropriate oligonucleotide primers that are specific to one or more microbe nucleic acid sequences that the sample is suspected of being contaminated with. Amplification products may then be further subject to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected microbe (determine parameters such as but not limited to the microbial strain, pathogenecity, quantity etc.).

As used herein "preparing" or "preparing a sample" or "processing" or processing a sample" refers to one or more of the following steps to achieve extraction and separation of a nucleic acid from a sample: (1) bacterial enrichment, (2) separation of bacterial cells from the sample, (3) cell lysis, and (4) nucleic acid extraction and/or purification and/or isolation (nucleic acids may be e.g., DNA, total DNA, genomic DNA, RNA). Embodiments of the nucleic acid extracted/isolated/purified include, but are not limited to, DNA, RNA, mRNA and miRNA.

As used herein, "presence" refers to the existence (and therefore to the detection) of a reaction, a product of a method or a process (including but not limited to, an amplification product resulting from an amplification reaction), or to the "presence" and "detection" of an organism such as a pathogenic organism or a particular strain or species of an organism.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

The presence or absence of an amplified product can be determined or its amount measured. Detecting an amplified product can be conducted by standard methods well known in the art and used routinely. The detecting may occur, for instance, after multiple amplification cycles have been run (typically referred to an end-point analysis), or during each amplification cycle (typically referred to as real-time). Detecting an amplification product after multiple amplification cycles have been run is easily accomplished by, for instance, resolving the amplification product on a gel and determining whether the expected amplification product is present. In order to facilitate real-time detection or quantification of the amplification products, one or more of the primers and/or probes used in the amplification reaction can be labeled, and various formats are available for generating a detectable signal that indicates an amplification product is present. For example, a convenient label is typically a label that is fluorescent, which may be used in various formats including, but are not limited to, the use of donor fluorophore labels, acceptor fluorophore labels, flourophores, quenchers, and combinations thereof. Assays using these various formats may include the use of one or more primers that are labeled (for instance, scorpions primers, amplifluor primers), one or more probes that are labeled (for instance, adjacent probes, TaqMan® probes, light-up probes, molecular beacons), or a combination thereof. The skilled person will understand that in addition to these known formats, new types of formats are routinely disclosed. The present invention is not limited by the type of method or the types of probes and/or primers used to detect an amplified product. Using appropriate labels (for example, different fluorophores) it is possible to combine (multiplex) the results of several different primer pairs (and, optionally, probes if they are present) in a single reaction. As an alternative to detection using a labeled primer and/or probe, an amplification product can be detected using a polynucleotide binding dye such as a fluorescent DNA binding dye. Examples include, for instance, SYBR® Green dye or SYBR® Gold dye (Molecular Probes). Upon interaction with the double-stranded amplification product, such polynucleotide binding dyes emit a fluorescence signal after excitation with light at a suitable wavelength. A polynucleotide binding dye such as a polynucleotide intercalating dye also can be used.

As used herein, a "non-MAP organism" is an organism of the *Mycobacterium avium* Complex (MAC) with the exception of *Mycobacterium avium* subsp. *paratuberculosis*. Non-MAP organisms include *Mycobacterium avium* subspecies *avium* (MAA), *Mycobacterium avium* subsp. *hominissuis* (MAH) and *Mycobacterium avium* subsp. *silvaticum* (MAS), as well as MAC organisms of indeterminate subspecies.

As used herein, a "non-MAP-specific polynucleotide" refers to a nucleic acid sequence that is able to specifically hybridize to a nucleic acid sequence that is present in a non-MAP organism and/or to a portion and/or complement thereof, under suitable hybridization conditions and which does not hybridize with other nucleic acid sequences that do not encode for a non-MAP-specific nucleic acid sequence. In some embodiments, a "non-MAP-specific polynucleotide" of the disclosure may be a probe or primer sequence specific to hybridize to a non-MAP target nucleic acid sequence. It is well within the ability of one skilled in the art, using the present teachings, to determine suitable hybridization conditions based on probe length, G+C content, and the degree of stringency required for a particular application.

It is expected that minor sequence variations in non-MAP-specific target nucleotide sequences associated with nucleotide additions, deletions and mutations, whether naturally occurring or introduced in vitro, would not interfere with the usefulness of primer and probe sequences disclosed herein in the detection of non-MAP organisms, as would be understood by one of skill in the art. Therefore, the scope of the present invention as claimed is intended to encompass minor variations in the sequences of the non-MAP specific target nucleic acid sequences described here and the non-MAP specific nucleotides, such as, exemplary primer sets and probe sequences set forth here, and all sequences disclosed also comprise sequences having at least a 90% sequence homology to these sequences.

A probe may be RNA or DNA. Depending on the detection means employed, the probe may be unlabeled, radiolabeled, chemiluminescent labeled, enzyme labeled, or labeled with a dye. The probe may be hybridized with a sample in solution or immobilized on a solid support such as nitrocellulose, a microarray or a nylon membrane, or the probe may be immobilized on a solid support, such as a silicon chip or a microarray.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, may depend upon, for example, the nature of the nucleotide sequence, temperature, and buffer conditions. These conditions may also depend on what event is desired, such as hybridization, cleavage, or strand extension. An "isolated" polynucleotide refers to a polynucleotide that has been removed from its natural environment. A "purified" polynucleotide is one that is at least about 60% free, preferably at least about 75% free, and most preferably at least about 90% free from other components with which they are naturally associated.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims. Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). The term "and/or" means one or all of the listed elements or a combination of any two or more of the listed elements.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Q.beta. replicase system (Lizardi et al., 1988, BioTechnology 6:1197 1202), and the techniques disclosed in WO 90/10064 and WO 91/03573.

Examples of techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), transcription-based amplification (Kwoh et al., 1989, Proc. Natl. Acad. Sci. USA 86:1173 1177) and restriction amplification (U.S. Pat. No. 5,102,784).

Other exemplary techniques include Nucleic Acid Sequence-Based Amplification ("NASBA"; see U.S. Pat. No. 5,130,238), Qβ replicase system (see Lizardi et al., BioTechnology 6:1197 (1988)), and Rolling Circle Amplification (see Lizardi et al., Nat Genet 19:225 232 (1998)). The amplification primers of the present invention may be used to carry out, for example, but not limited to, PCR, SDA or tSDA. Any of the amplification techniques and methods disclosed herein can be used to practice the claimed invention as would be understood by one of ordinary skill in the art.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent®. (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

Those having ordinary skill in the art, in light of this specification, will understand that many modifications, alternatives, and equivalents of the embodiments described above are possible. All such modifications, alternatives, and equivalents are intended to be encompassed herein.

EXAMPLES

The following procedures are representative examples of embodiments according to the disclosure that may be employed for the detection of a non-MAP organism. These examples are not intended to be limiting to the scope of the claims and/or the disclosure in any way.

Example 1

Compositions & Methods to Detect Non-MAP Organisms

The present example describes exemplary assays designed to detect non-MAP organism using probe and primer sequences designed as described herein. The assays disclosed herein can be used in diagnostic methods and kits to detect a non-MAP organism in a sample, such as for example a sample obtained from an animal suspected of being infected with a non-MAP organism, with no cross-reactivity to a MAP organism.

Table 2 lists a set of TaqMan® primer/probe sets, where primer sequences comprise sets/pairs of primers, each primer set including a forward and a reverse primer, and a corresponding probe sequence, that have been shown to be specific to the amplification of non-MAP organisms with a CT cutoff of 40.

TABLE 2

| ASSAY ID Number | FORSEQ | REVSEQ | PROBESEQ | Forward coord | Probe coord | Reverse coord | Target gene | Gene product | Amplicon length |
|---|---|---|---|---|---|---|---|---|---|
| 62324 | CGGATCGCCCAGTGCAA SEQ ID NO: 9 | GGCAGCTCGGCCTGT SEQ ID NO: 10 | TCGTGCGCATCGACGGCC SEQ ID NO: 11 | 3364286 | 3364320 | 3364352 | MAV_3242 | actinomycin synthetase II | 67 |
| 62325 | TGGCGCAATCTGTCATCGA SEQ ID NO: 12 | CGCCTTGGTGCCACTCAT SEQ ID NO: 13 | CGCCGCCGCATCTGATTTCC SEQ ID NO: 14 | 4964390 | 4964419 | 4964468 | MAV_4831 | hypothetical protein, adjacent to tRNA | 79 |
| 62333 | GGCTGCACCCGAGGA SEQ ID NO: 15 | GCGGGCTGATACTCCACATC SEQ ID NO: 16 | CCAAACCTTGGCAGGTGTTGGCAC SEQ ID NO: 17 | 318346 | 318361 | 318426 | MAV_0328 | hypothetical protein | 81 |
| 62348 | GCGCGGTGACGTTGTG SEQ ID NO: 18 | GTTCAAGGAGCAGTACACCAAGT SEQ ID NO: 19 | CAGCGCCGAGCTGGCCCA SEQ ID NO: 20 | 5122763 | 5122780 | 5122821 | MAV_4975 | probable conserved membrane protein | 59 |
| 62350 | TGCGCAAGCCAGATGTCTAG SEQ ID NO: 21 | GAAAGGCAGACCCTGTGGTT SEQ ID NO: 22 | ATGCTCAAGCACTTCCGCTTACGC SEQ ID NO: 23 | 3364379 | 3364407 | 3364470 | MAV_3242 | actinomycin synthetase II | 92 |
| 62328 | GGCCTGGTATACAACCAACGA SEQ ID NO: 24 | GAGCGTGGCCGTGGAT SEQ ID NO: 25 | TCAACTGCGACAGCAACTGGTTCC SEQ ID NO: 26 | 318727 | 318765 | 318819 | MAV_0328 | hypothetical protein | 93 |
| 62330 | AGCAGCATCGGATTGACCAT SEQ ID NO: 27 | ACGCGTGGGTGACGAC SEQ ID NO: 28 | ACCACCGAGCCGACCAGATACA SEQ ID NO: 29 | 3228898 | 3228928 | 3228967 | MAV_3140 | possible drug efflux membrane protein | 70 |
| 62335 | CCCAGGATCGCGACGAC SEQ ID NO: 30 | GGCGCACTTGCTGATTCA SEQ ID NO: 31 | CTGCTGGACCGTTCCGCCGA SEQ ID NO: 32 | 3357197 | 3357218 | 3357289 | MAV_3239 | syringomycin synthetase | 93 |
| 62338 | CTGGCCGGCAGATAGATCAG SEQ ID NO: 33 | GCCTTGCGGGACAGC SEQ ID NO: 34 | CCGACGGCTTGTCCGGGTCGAATC SEQ ID NO: 35 | 5006970 | 5007010 | 5007049 | MAV_4873 | pmethyl-transferase, putative, family protein | 80 |
| 62339 | GGTGGTCAGGAACTCATTCGT SEQ ID NO: 36 | GGGCGCCAGGTATCTGA SEQ ID NO: 37 | TAGAGCGCCACCCCGCCGG SEQ ID NO: 38 | 3229014 | 3229039 | 3229092 | MAV_3140 | possible drug efflux membrane protein | 79 |

TABLE 2-continued

| ASSAY ID Number | FORSEQ | REVSEQ | PROBESEQ | Forward coord | Probe coord | Reverse coord | Target gene | Gene product | Amplicon length |
|---|---|---|---|---|---|---|---|---|---|
| 62344 | GGGCGAACC GGAACAAC SEQ ID NO: 39 | AGCGGCCT GGACGAC SEQ ID NO: 40 | CTGGCGATCCA GCGCACGCC SEQ ID NO: 41 | 3364077 | 3364112 | 3364173 | MAV_3242 | actinomycin synthetase II | 97 |
| 62347 | CGGCCCGCT GCTGA SEQ ID NO: 42 | GAGGAGTCTT CGGCCATGAC SEQ ID NO: 43 | TTCGCCCC GGAGGTCC ATTCCAC SEQ ID NO: 44 | 5006385 | 5006404 | 5006465 | MAV_4872 | ppe family protein | 81 |
| 62353 | CGGGCAGGG TGAACGT SEQ ID NO: 45 | TGTTCGCCGG CTTCGA SEQ ID NO: 46 | CCCAGGA CCCGGTC GAGCTC SEQ ID NO: 47 | 3104524 | 3104558 | 3104613 | MAV_3056 | Linear gramicidin synthetase subunit D | 90 |

*Assay ID describes an assay comprising using Forward Primers and Reverse Primers described in one row and in some embodiments Probe described in the same row.

An exemplary method of detecting the presence of a non-MAP organism in a sample, comprises: 1) isolating nucleic acid from a sample suspected to contain a non-MAP organism; and 2) detecting the presence of at least one non-MAP-specific target nucleic acid and/or fragment thereof and/or complement thereof as shown using an assay described in Table 2 above comprising using for example a set of primers, comprising a forward and a reverse primer described in a row to amplify the at least one non-MAP-specific target nucleic acid and/or fragment and/or complement thereof; and detecting the amplified product. In some optional embodiments, a probe described in the same row can be used to detect an amplified product amplified by forward and reverse primers from the same row. Such a method can be a diagnostic method, where a sample can be derived from a mammalian animal or a human suspected of being infected with a non-MAP organism.

As shown in Table 2, an Assay ID Number (such as 62324, 62325 etc.) is assigned to describe an associated primer pair and associated probes that can be used for amplification and/or detection of a target non-MAP sequence (such as in non-limiting examples SEQ ID. NOs: 1-8, Table 1) and/or fragments and/or complements thereof. These specific combinations of primer pairs and probe sequences have been designed to selectively amplify non-MAP specific target nucleic acid sequences. In some embodiments these primer pairs are degenerate.

In some embodiments, multiplex assays can be performed by simultaneously contacting a sample with one or more primer pairs as set forth herein. Multiplex assays can be performed in parallel or sequentially.

Each of the assays was tested against the 16 sequenced *Mycobacterium avium* strains confirm diagnostic sensitivity and specificity. For every assay the forward primer, reverse primer and probe were diluted in a mix to 500 nM for each primer and 250 nM for the probe. 5 µL of sample DNA (18-39 ng of total nucleic acid) was input into a 20 µL qPCR using the Path-ID™ qPCR master mix and each candidate non-MAP assay. The thermal profile and qPCR set-up is shown below in Table 3.

| Non-MAP qPCR Master Mix | |
|---|---|
| 20 µl | reaction volume |
| 1X | Component |
| 5 µl | Sample |
| 4.00 µl | NF H20 (9937) |
| 10.00 µl | 2X PCR Master Mix |
| 1.00 µl | 20X Primer Probe Mix |
| 20.0 µl | total volume |
| Standard Thermal Profile | |
| 1. 95dC: 10 mins: 1Rep | |
| 2. 95dC: 15 sec | |
| 60dC: 60 sec | |
| 40 Reps | |

Table 4, below, has results of sensitivity and specificity testing. There was no cross-reactivity with any MAP strains (with a CT cutoff<40 considered positive).

TABLE 4

| Assay ID No. | MAS Pigeon 49884 | MAA Elephant 10-5581 | MAA Hawk 10-9275 | MAA Duck 11-4751 | MAA Broadbill 05-4293 | MAH Deer 10-4249 | MAC Pig 10-5560 | Unknown MAC Dog 09-5983 | Unknown MAC Deer 11-0986 | MAH Pig 10-5606 | MAP Bison 10-4404 | MAP Bison 10-5975 | MAP Cattle 10-5864 | MAP Cattle 10-8425 | MAP Sheep 08-8281 | MAP Sheep 11-1786 |
|---|---|---|---|---|---|---|---|---|---|---|---|---|---|---|---|---|
| 62324 | 22.07 | 22.46 | 23.80 | 21.93 | 22.32 | 22.38 | 23.34 | 22.53 | 24.16 | 23.97 | 40.00 | 40.00 | 40.00 | 40.00 | 40.00 | 40.00 |
| 62325 | 20.12 | 21.56 | 21.58 | 19.34 | 20.41 | 25.36 | 20.55 | 20.59 | 21.57 | 22.16 | 40.00 | 40.00 | 40.00 | 40.00 | 40.00 | 40.00 |
| 62328 | 21.00 | 22.40 | 22.50 | 20.18 | 21.21 | 20.99 | 21.26 | 21.12 | 22.69 | 22.04 | 40.00 | 40.00 | 40.00 | 40.00 | 40.00 | 40.00 |
| 62330 | 20.55 | 22.41 | 22.17 | 20.36 | 21.39 | 20.88 | 21.63 | 21.53 | 22.63 | 22.59 | 40.00 | 40.00 | 40.00 | 40.00 | 40.00 | 40.00 |
| 62332 | 23.10 | 32.45 | 24.62 | 22.24 | 23.00 | 31.21 | 31.60 | 23.20 | 25.09 | 23.10 | 40.00 | 40.00 | 40.00 | 40.00 | 40.00 | 40.00 |
| 62333 | 21.82 | 23.05 | 23.34 | 21.15 | 22.01 | 21.46 | 22.40 | 21.95 | 23.49 | 22.60 | 40.00 | 40.00 | 40.00 | 40.00 | 40.00 | 40.00 |
| 62335 | 21.61 | 22.91 | 22.82 | 20.97 | 21.78 | 21.43 | 22.52 | 21.94 | 23.24 | 23.12 | 40.00 | 40.00 | 40.00 | 40.00 | 40.00 | 40.00 |

TABLE 4-continued

| Assay ID No. | MAS Pigeon 49884 | MAA Elephant 10-5581 | MAA Hawk 10-9275 | MAA Duck 11-4751 | MAA Broadbill 05-4293 | MAH Deer 10-4249 | Unknown MAC Pig 10-5560 | Unknown MAC Dog 09-5983 | Unknown MAC Deer 11-0986 | MAH Pig 10-5606 | MAP Bison 10-4404 | MAP Bison 10-5975 | MAP Cattle 10-5864 | MAP Cattle 10-8425 | MAP Sheep 08-8281 | MAP Sheep 11-1786 |
|---|---|---|---|---|---|---|---|---|---|---|---|---|---|---|---|---|
| 62338 | 21.21 | 23.05 | 22.89 | 21.33 | 22.28 | 22.30 | 22.40 | 22.90 | 23.23 | 23.79 | 40.00 | 40.00 | 40.00 | 40.00 | 40.00 | 40.00 |
| 62339 | 20.77 | 22.28 | 22.04 | 20.33 | 21.15 | 21.09 | 21.67 | 21.34 | 22.65 | 22.56 | 40.00 | 40.00 | 40.00 | 40.00 | 40.00 | 40.00 |
| 62344 | 21.27 | 23.66 | 23.35 | 21.47 | 22.19 | 22.01 | 23.00 | 22.84 | 24.73 | 24.03 | 40.00 | 40.00 | 40.00 | 40.00 | 40.00 | 40.00 |
| 62345 | 23.37 | 25.88 | 25.75 | 24.10 | 24.19 | 24.80 | 25.96 | 24.91 | 25.56 | 24.50 | 40.00 | 40.00 | 40.00 | 40.00 | 40.00 | 40.00 |
| 62347 | 20.89 | 22.12 | 22.09 | 20.11 | 21.07 | 20.89 | 21.46 | 21.41 | 22.48 | 21.84 | 40.00 | 40.00 | 40.00 | 40.00 | 40.00 | 40.00 |
| 62348 | 20.47 | 22.42 | 22.01 | 20.41 | 21.48 | 21.28 | 21.97 | 21.75 | 22.58 | 22.78 | 40.00 | 40.00 | 40.00 | 40.00 | 40.00 | 40.00 |
| 62350 | 21.84 | 23.32 | 23.25 | 21.37 | 22.06 | 22.35 | 22.67 | 22.14 | 24.03 | 23.89 | 40.00 | 40.00 | 40.00 | 40.00 | 40.00 | 40.00 |
| 62351 | 20.68 | 21.99 | 22.24 | 19.94 | 20.90 | 20.70 | 21.36 | 20.68 | 22.83 | 22.83 | 40.00 | 40.00 | 40.00 | 40.00 | 40.00 | 40.00 |
| 62353 | 20.74 | 22.71 | 22.28 | 20.71 | 21.66 | 21.20 | 21.95 | 21.59 | 22.78 | 23.81 | 40.00 | 40.00 | 40.00 | 40.00 | 40.00 | 40.00 |

Figure 2:
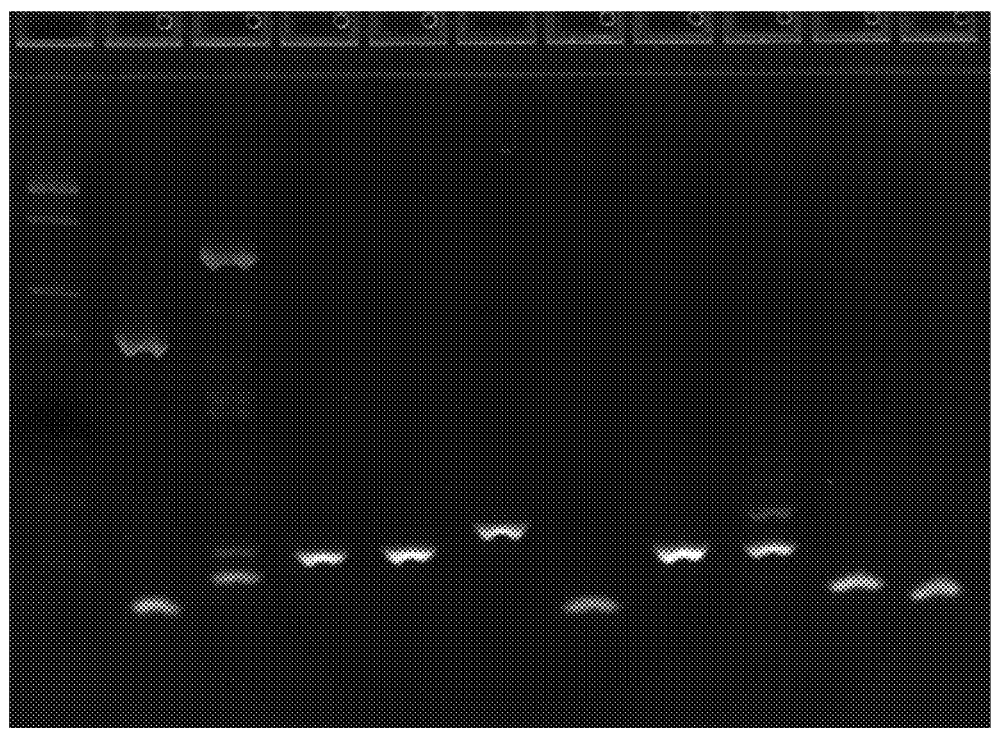
FIG. 2 illustrates a gel electrophoresis profile, according to one embodiment of the disclosure.
Figure 3:
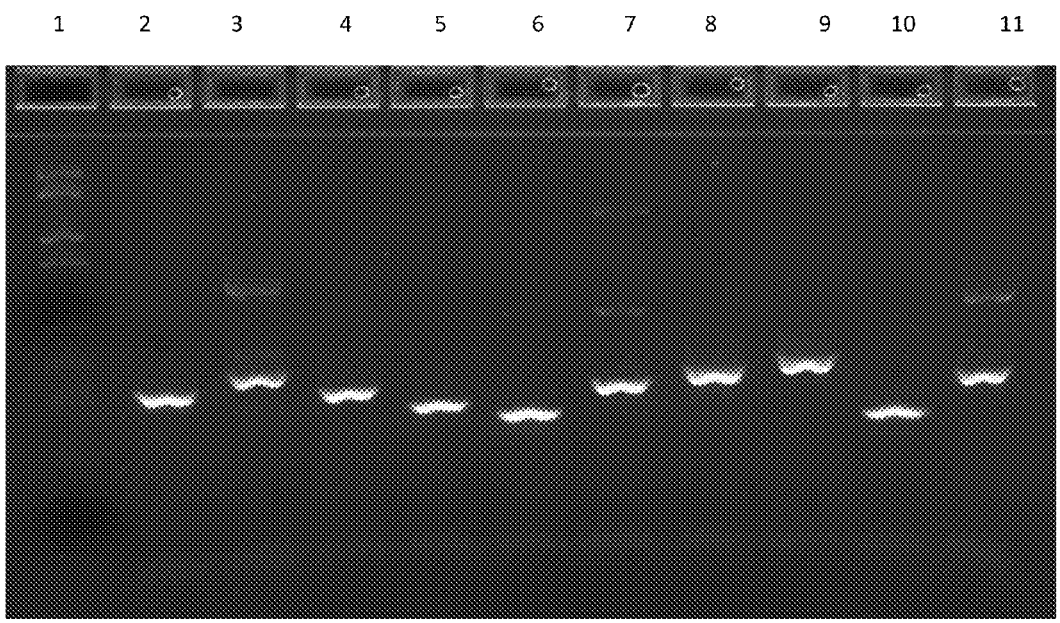
FIG. 3 illustrates a gel electrophoresis profile, according to one embodiment of the disclosure.

FIGS. 1-6 depict electrophoresis gel profiles and results for the assays conducted and Assay ID numbers on the gel profiles are as shown in Tables 2, 3 and 5 and correlate to the probe and primers used in Table 3 and the targets in Table 2. FIGS. 1-3 depict results of assays tested against an MAH sample. The thermal profile and qPCR set-up are as described in Table 4. 15 μL of amplified product was run on a 4% agarose gel for 30 min. FIG. 1 shows an electrophoresis profile for assays with ID numbers 62321-62330 for a sample with MAH and lanes numbered 4, 5, 9 and 11 show assays with 100% sensitivity and specificity. FIG. 2 shows an electrophoresis profile for assays with ID numbers 62331-62335, 62337-62339, 62341 and 62342 for sample with MAH and lanes numbered 4, 6, 8, and 9 show assays with 100% sensitivity and specificity. FIG. 3 shows an electrophoresis profile for assays with ID numbers 62344-62353 for sample with MAH and lanes numbered 2, 5, 6, 8 and 11 show assays with 100% sensitivity and specificity.

Figure 4:
FIG. 4 illustrates a gel electrophoresis profile, according to one embodiment of the disclosure.
Figure 5:
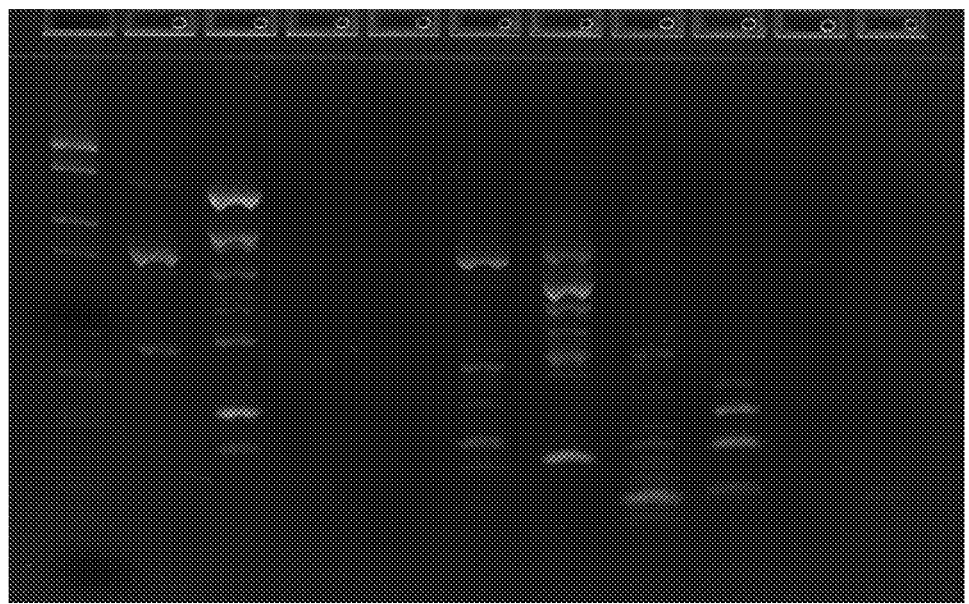
FIG. 5 illustrates a gel electrophoresis profile, according to one embodiment of the disclosure.
Figure 6:
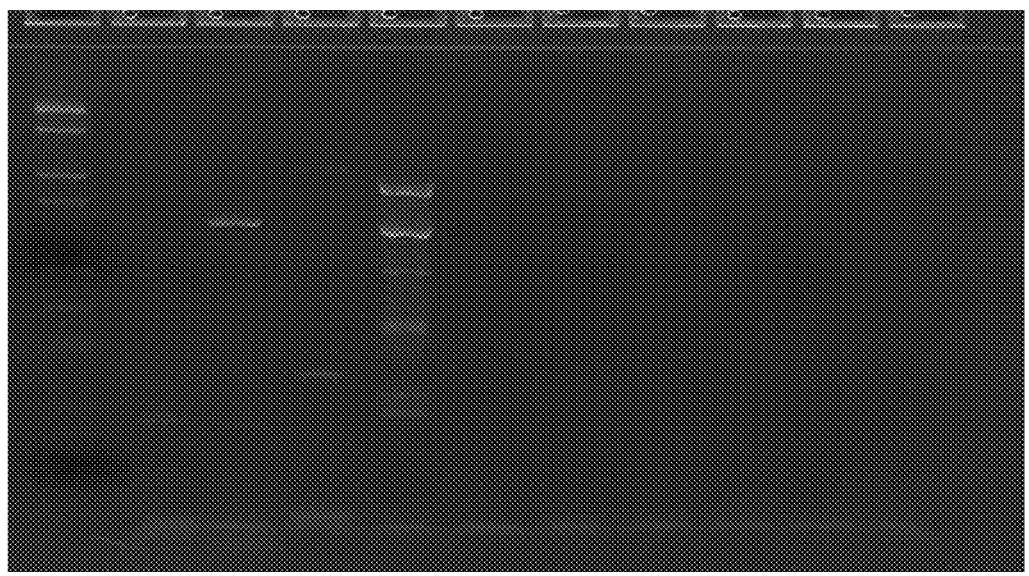
FIG. 6 illustrates a gel electrophoresis profile, according to one embodiment of the disclosure.

FIGS. 4-6 depict results of assays tested against a MAP sample and no cross-reactivity was seen with MAP. The thermal profile and qPCR set-up are as described in Table 4. 15 μL of amplified product was run on a 4% agarose gel for 30 min. FIG. 4 shows an electrophoresis profile for assays with ID numbers 62321-62330 for a sample with MAP and lanes numbered 4, 5, 9, and 11 show assays with 100% sensitivity and specificity. FIG. 5 shows an electrophoresis profile for assays with ID numbers 62331-62335, 62337-62339, 62341 and 62342 for sample with MAP and lanes numbered 4, 6, 8, and 9 show assays with 100% sensitivity and specificity. FIG. 6 shows an electrophoresis profile for assays with ID numbers 62344-62353 for sample with MAP and lanes numbered 2, 5, 6, 8, and 11 show assays with 100% sensitivity and specificity.

The above experiment demonstrates the feasibility of using the assays described herein as a specific and highly sensitive detection method for detecting a non-MAP organism and not cross-reacting with a MAP organism. In some embodiments, the disclosure provides a set of highly-specific TaqMan® assays for the detection of non-MAP organisms and excluding the detection of *Mycobacterium avium* subsp. *paratuberculosis*.

One or more advantages of the methods of the present disclosure are described in the following section. Each individual assay can independently serve as a highly-accurate diagnostic assay for non-MAP detection. Each assay has the advantage of targeting single-copy gene in a non-MAP genome instead of genomic insertion sequences that are able to mobilize between genomes and insert into the genome of new species, making them suboptimal for a species-specific assay.

The currently described assays and methods are able to detect non-MAP organisms in multiple host species including ruminants such as sheep, cattle, bison, deer, pigs, dogs, elephants, hawks, and several other animals quickly and accurately with no cross-reactivity to MAP which is a very closely related *M. avium* subspecies, making it ideal for veterinary diagnostics.

While the foregoing specification teaches the principles of the present invention, with examples provided for the purpose of illustration, it will be appreciated by one skilled in the art from reading this disclosure that various changes in form and detail can be made without departing from the spirit and scope of the invention. These methods are not limited to any particular type of host organism, type of sample or nucleic acid contained therein for e.g., total genome DNA, RNA, cDNA and the like can be analyzed using some or all of the methods disclosed in this disclosure. This disclosure provides powerful tools for analysis of complex nucleic acid samples from a variety of animals. From experiment design to detection of non-MAP microbes, the above disclosure provides for fast, efficient and inexpensive methods for detection of pathogenic organisms.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

TABLE 5

SEQ ID NO: 1:
CCCAAGCGGGCCAATCGGTTTACCGCGGCACTCCCTTGCCGAGTCGGCGGTTGGATAGTGTA
CTTGTCCACGTGGAGGGAAGCAGCTGGTGACTGTCCGGCGCGGTTTCGGTCGTGCACCGGCG
GGACTCTGCGTTGCCGCAGCCCTTGTTCTCAGCGGTGGCGCGTGCGCAACGCATAAGCAGCA
GCCTGCCGCGGCTCCAGCAACCCTTAGGGCTGCGCCCGATCAACTCGGGCCGTGCGCGCCGG
ATCGGTTGGCGCGCTGCGTACCCGGGCTGGCTGACGTCGACGAGAACCTCTTCGGCGGCGTC
GCTGCGTACCAGCCTGATCCAGGCTTCGCCTCGGTGCCGCCCTCGGCCGCTCGGGAGGCTGC

TABLE 5-continued

```
ACCCGAGGAGTGCCAACACCTGCCAAGGTTTGGCGCCCAGGCCGGTCGCGAACTCGATGTG
GAGTATCAGCCCGCGAGGGACACCAACGGGAGGCCTTTAAGCAACCGGTTCCCGGCCAATG
GTGGCGATTACGTTCGACTTCGGTTCACGGTCGCCGGCGACGGCGATGATATCGGGACTGCG
ATGGCGGCGTGGGCCCGTCGATGTCCGATGTGGGCCGTGCCCAGTCGATGAATGACAGCG
GGATCCAGGGCTGGCTCGTCGCCGAGTCCGGCGAGCACCTGAGCCGGTACCAATCGGGCGA
TGTCGCGTCGCAGTGGCCCTATGTCTCGAACACGGCAGCGGTAGTGCTACCCAACAAGGTGA
TCGTCCAGGCCTGGTATACAACCAACGACCCGTCCGCCGCATCGCGGAACCAGTTGCTGTCG
CAGTTGATCGGGGCGTCTGGGCATCCACGGCCACGCTCTGCTCTGCCGCCCAAACTCGCCGA
CTGGAGCCAAGCGCAGATCTCGACGCTGCTTCCTG

SEQ ID NO: 2:
GTGGTGCGGCCCTCGAAGGTCACCGCCGGCGCTTGCGGGCTGCGCTGTGCCTGCGCGGTGAA
CAGCGCCGGGATCGACGTCCGGGTGGCGGGCCGGTCGAGGACCGCCCGGGCGCCCCAGTCG
TGCAGCCGCTGGTGTTCGGCCGGGTCGAGCACGTCGATCGACGACAGCGGCCGTGCCGGGT
CGGCGGTCATGGCGACCAGTACCCGCCGCATCCGCTCGATCAGCGTCGCGATGTCCTCGTCG
TCGAAAACCCGTGTGGCGTATTCGATTTGGAGGCGCAGCTGCGACCCGGGCTGGGCCTGCAC
GGTCAGCGGGTAGTGGGTGGATTCGCGGCTGGTGATGTCGGTGACGGCCAGCTCCTGGTCGC
CGGACAGCGCGCCGGCGTCGATCGGGTAGTTCTCGTAGGCGAACAGCGTGTCGAAAAGCTT
GTCCTGGCCGGTGATTCGGTGGATCTCGTTGAGCGCCAGGTGCTGGTGGTCGAGCGTGTGGT
TGTAGGCGCCTTGCAGCTGGTGCAGCAGGTCGACGGTGCTGGTGGTCGCGGTGATGTTCGCC
CGCACCGGCACGGTGTTGATCAGCAGGCCCACCATCGTGTCGGCGCCGGGCACCTCCGCGG
GCCGGCCCGACACCGTGGTGCCGAAGACGACGTCGCGTTGCCCGGTGAGGGCGCACAGCAG
GCGCGCGAACGCCGCCTGCAGCACGGTGTTGACGGTGGTGTGGCAGGACCGGGCCAAGTCG
GTGACGGCCCGGGTCAGGTCGGCGGGCAGGGTGAACGTCTCGACCTGTTGCGGCCCGAGCT
CGACCGGGTCCTGGGGCCCGACCAGGGTCGGGGTGTCGAAGCCGGCGAACACCTCGGCCCA
CGCCGCGCGGGCGGCGTCGAGGTCCCGTTCGGCCAGCCAGTCGACGAAGCGCGGTAGGGC
GCCGGCGCCGGAAGCCGCTGACCGTAGTAGGCGGCGAAGATCTCGCCCAACAGGATCGGCA
TCGACCAGCCGTCCAGCACGATGTGGTGGTTGGTCAGCAGCAGCCGGTGCCGGTCGGTCGCG
GTGCGCACCAGCGCCACCCG

SEQ ID NO: 3
GCCCAGCAATCAAAACATGCATATCGGGTGCCGCACCGCAAACCAGGCTGGCGACGCCGAA
CACGGCCAGCCCCAGCAGATACGACGCCCGCGCGCCGACGCGCAGCAGCATCGGATTGCN
ATGGTGGCCGCGACCACCGAGCCGACCAGATACAGCGTCGTCACCCACGCGTAGAGCCGAC
TGCCGCCGATCTCGGCGATGGTGTTGGGCAACAAGCTGGTGGTCAGGAACTCATTCGTGGCG
TAGAGCGCCACCCCGCCGGCGAGCAGGATCGAGGTCCTCAGATACCTGGCGCCCAGCAGCT
CTCGCCAGCCGCCGGTGATGGTCGCCGCATCCGTCACCCCTCTA

SEQ ID NO: 4
TGCCAGCGAATGGCACTGGCTCCACACCTGATCCGGTCCCAGGGTGATGCCGGTGTCCAGCG
ACGCGAACAGTTGGGTGATGTTGCGGTGGCTGACGGCCACTCCCTTGGGTTCGCCGGTGGTG
CCCGAGGTGTAGATCACGTGGGCGATGTCGCCGGCGGCCGGCCCGGGCCGGCCGGTTCGG
TGGCCGGGTAGTCCGCCAACGCCGGATCGTCGAGGTCGACGATCGCCGCGCCGAGCCCGGT
CAGCCGGGAGCGCGATCCCGCATCGGTCACCACCACCCGCAGATCGGCGTCGGCGACGATG
AAGGCTATCCGCCGCCGGCACCGCCGGATCCATCGGCACGTACGCCGCGCCCGCCTTCAG
TACCCCCAGGATCGCGACGACCGCCTCGGCGGAACGGTCCAGCAGCAACCCCACGTACTGC
CCCCGGTCCACGCCGTGCTGAATCAGCAAGTGCGCCAGCCGATTCGCTGTCTCGTCGACCTC
CCGATAGGTCCAGCAGCGGTCCGCGCTGCTGATCGCCACCGCCCCGGCACCCGCTGCGCCC
AGGCGCCGAACAGCGCGGGCACCGAGGCGCCCGTCGTTGACCGGCCCAGCGCCGCGCGGTT
GCCGAATATGTCGAGCCGGGCAAACTCGGTGTCCTCGAGCACCTCGATCGACGAGAGGTGC
CGGCCCGGGTCGGCGGTCAGGACGTCGAGCACCCGGCGCAGCCGCTCGGTGAGGGTGCGGA
TGGTGTCCGCGTCGAAGACGTCGGTGCGGAATTCCACCGTTCCGGCGATGCCGGCGGGCCGG
CCCTCCTCGGTCCAGCGTTCGCACAGGGAGAAGGTCAGATCCATTCGAGCGGTGCCGATGTC
GATCGGCAGCGCCGCGACCTCCAGCTCGCCCAGGCGCAGCCGCGTCGGATCGTCGCCGCGC
CAGGTCAACATCACCTGAATCAGTGGGTGGTGGGCCAGCGATCGGGTGGGGTTGAGCCGCT
CGACCAGGATTTCGAAGGGCACGTCCTGGTGTTCGTAGGCGGCCAGGCTGCGTTGGCGCACC
CGGGCCAGGATTTCGCCGACGGTGGGATCACCGGACAAATCGACGCGCAGCACCAGGGTGT
TGACGAAGAACCCGACCAGGTCATCAAGAGCCGGGTCACCACGCCCGGCAATCGGAAAACC
CACCGCCACATCACAACTCGCACCGAGCTTGGCCAGCAGCACCGCCAAGCCGGCCTGCACC
ACCATGAAACTGGTCGCGTTATGCACCCGGGCCAGGGCCGATACCTGCTGCTGCAGCGACGC
CGGCCAGTCGATGTCCACCCGAGCCCCACGATGATCAGCCACCGCCGGATACGGCCGATCC
GTCGGCAACGCCAACCGCTCGGGCAACCCGGCCAACGCCTCCTG

SEQ ID NO: 5
TGGTTTCGGGCGGAAGGTTCGCCAGCCAGTAGGCCTCGTCGTCGCGGTAGTCGGCCGAGGAT
TCGTAGTGCGACTCGCACTCGACCAGCTCCCGCAGCGAGCCGAAGACGGCCGTCGGGATGG
GTCCGGCGGCGACGATCGCGGAGTAGATGGAGGCGATGCGGTGACCGACCAGCCCGACGCC
GGTGCCGTCGATGACGATGTGGTGGCAGCAGGCGAACAAGTAGAACTGGTCCCGCCGGGTC
GCAAAGAGGGCGAACCGGAACAACGGCCCGGACAGCGGCATCGGCGTGCGCTGGATCGCC
AGCGCCCGGCGGCGGGCCTCGGCCACCGGGTCGTCCAGGCCGCTCAGGTCGTCGAAGGTCA
GCTCGACGTCCGGATGCTCGATCGCCCGCTGGTAGACCGCCGCGTCCACCTCGAAGAACGCG
ACACGGGCGGGTTCAGCCTCCTGCACCGCCTGCCGGATCGCCCAGTGCAACGCGTCGCGCTC
GACGCGGCCGTCGATGCGCACGAACAGGCCGAGCTGCCACTCGGTGCTGGAGTGACCCGTT
GCCTGCGCAAGCCAGATGTCTAGCTGTCCGCGCGTAAGCGGAAGTGCTTGAGCATCAAGCTC
CATCCATCTCCCCAACCACAGGGTCTGCCTTTCAACCCCCCGGTTGATGAAGCCGCTCGAGC
AAGTGTTCTCTACCCGGTGCGGCCCCGGCGCGCGGCGCGATCCGCTCTGCCGTGCTCCACCC
GGCGACCGGCTGGAGCGCCGGCAAAGACGGACCGCAACCGTGGCTGCCCTCGTGGTGGACC
GAGGCGGCGAAGCCGGCGGCTGTCGCCACCGAATGCTTGGCGCTCACCGACTCCCAAGGCC
TCGTAGTCAACACGAGTGCAACAGTTGGGAAGGCTAGTAGACGACAACCCCGCTGGTCCAG
AGTTATTCAAACTTAATGTCCTGTGA
```

TABLE 5-continued

SEQ ID NO: 6
CCCATACTCCGGGCAACGGCCCAAGTTCTCGGCATCGCCAACGGCGACGCCGGCCTGCATCA
CAACCCGCGCACGGGTTTCCGCGTCACCAATCAGGGTGAGTTGTACGGCGTCGCAACCTTGG
CTTAGGTGTCAAAAAACGGTGAAGAAGGCTGCGGTGGCTGGCCATCTGACGATGCAGTTG
GAGGCGATGGCGTCGGCCGCACACATCCTGACAAACCAAGCCGACGGCTTCAGCAGCGAAC
TCGACAGCATCGCCGACGACTGGCGCAATCTGTCATCGACGTGGCAAGGCGCCGCCGCATCT
GATTTCCGGCCCGCATGGGATGAGTGGCACCAAGGCGCAAAGGCCGTCGCAACGCTGCTAT
CGGAACACTCCCAGCTGTTGCTCCGCTCACTGGACCTCATGCTCGACCACGAGACGATTGCC
GCGAGAGCCTTCGCCGCCCTGTCCCCAACGGATCCGGAATCATGAGCGCGCCGTTACACGGTC
GACCCTGAGGCACTGTCGCATTTTGCCGACCGACTGGCGAAATTCACTGCCAGCGCGGAACA
AATTGCCGCGGCCGTCGACCAATGCATCGCCGAACTCCACGGTTCCTGGCTGGGTCGCGGCG
CAGACGCCGAGCGCGAGTACCACCAAAGATGGGTAGCAGCCGACAAACAAATGCGAGAAG
CGCTCACCGAATTGCGCACCAATGTGGAGAGGGCGCACCGCAACTATGACGGTGTGGCCCA
ACACAATAC

SEQ ID NO: 7
CCACGCCAGATAGGGCGCGTGCGCGGCAACGTACCGCTCGGCGCTGGGCCCCTGCCACGCA
TCGGATTGCGCCGCCGCCAGCGTCGCGCTGAGTTCCGCGGCGGCCGACGCATAGGTTTCGCT
CAACGACGTCCAGGACGCGGCCGCGCTCAGCAGGCCGGCCGGTCCCGGCCCGCTGCTGAGC
AGCGTGGAATGGACCTCCGGGGCGAACGCCATCCACACCGGCGCGGTCATGGCCGAAGACT
CCTCGTCGGGCTGGGTCAGGAACCGCCGGGGCTGTTCGGCGGCGCACGGGTCAGCCCGGTA
GTAGTCGCACCGGGGCGCGAGAAGTTCCGGCGGCGCCGATTCATGGATGACTCATGAA
AAACCGGCCGCGATCGGGGTTCGCGGCCGGTTTGTCGCTCGGCGGGTCAGGCCCGCACGGC
GCTCACCAGGGTGTTGCGCGCGATCATCGGCCCGGCCTCGGTGTCCGGGCCGGGCACCGGAC
GGCCGACCTGGCGCAGGTAGTCGGCCAGCGGGGTGGGCACCGCGGTCCAGCCGCGGCTGCC
GAACCACTCGGCGGCCGGCGCGCACTGTTCGTTGTAGACGAGCTGAAAGAACATTCGCTGCT
CGCCCTGCTCGTTGGCGGCGCGTTCGGCGGCCACCGCGGCCTCGAAGTCCTGGGCGTCATC
GGGGCGCCCTCCTCGACCGCGACGTGGCTGCCGTGGCCGGCCAGCGCGTCGATGCCGGTGA
ACAGCTGCTCCTGGGCGCTGGCCGGCAGATAGATCAGCAGGCCCTCGGCGATCCACGCCGA
CGGCTTGTCCGGGTCGAATCCGCTGTCCCGCAAGGCCTGCGGCCAGTCCTCGCGCAGATCCA
CGGCGATCTCACGGCGCTCGGCGCGCGGGTGGGCGTCGACGCC

SEQ ID NO: 8
GGGTCACCCGCAGGATCACCGCCACGCTGGCCGCCGCGGGGCCGAGGGCCTCGACGCCGGC
CGACACCGTGGCCGCCTGCGCGGTGACGTTGTGCTGGGCCAGCTCGGCGCTGGACTTGGTGT
ACTGCTCCTTGAACGCCGCGGCGTGTTCGGGCACCACCATCGCCGCGGCCCGGTCGATGGCG
CCGGTCGGTGCGGTCGGGCTGAACGAGGCCATCGACTCGGCCATGCCGGTGGCGATCGCGA
CGACCTTGTGGGAGTCGTCGGTGAAGTCACGGTCGGCCCTGGTCCAGTGCGTGTAGCCGGTC
GCGACGGCCGCCGCCAGCGCGGCCGTGCACAGCAGCACCACCGCCAACCGCAGCCCCGGCG
CGTCGTCGTCGGTGCCGAGGCTGACCGAATCGCGGCGCAGCAGCCAGAAATTGATCAGCAC
GCCCTCGACGATCAACAACACCAGCACCGAGCAGGCCGACACCCACCACAGCGGCCAGCCG
AGCACCACGCCGATGGCCAGCAGGGCGCAATCGCGGCCACCGGGGCCGCGATGTCGAAGG
CGAACAACCGCCAGATGTTTCTCATCGCATCTCTCACCTGATCGAGGACAGCCCGGAGATCA
TCAGCTTGCCGTCCACGTCGGAGACGTCCAGGCGCAGGCTCCAGTGCACGGTCTGCGGCTTG
GCGCCGACGTTTTCGCTCACCGAGGTGGCGACCAGCAGCACCGAGTCGGTGCGGGTGGCGA
ACGGCGGCAGCTTGGTGGTGACCGGCGGCCGCGCGGCGCCCGGCTGGGCGTCCAGGTCGTG
GTGCACGGTTTCGATCGCCACCGCGTCCACCCGCCCGCTGCTCTTGGACTGCAGCTTCTCCAC
CACCGCCCGGTAGGGCTGCACCGCGGCGTCGAAGTCGGTGTTGAGCTCGCCGACCGTGCCGT
CGTGCAGCCGCTGCAGGCTGGCGTCGACGTTGCCGCTGTTCATGTTGATCAGCACGTTCGCC
CAGTCCGCGGCGGTTCCGCATGACCCGGCTCAAATAGCTGCGCTCGGCGACCTGGTCGCGGTG
GTCGGACCAGATCAGGGCGGCGAGCACCACCGCGGCCACGGACAGCACGCCGAGAACCGTT
GAGGCGACGCCGTAATGGGAGAAGATTCGGCCGTCCGCGGCTTGGGCGGTTCGTCGGCAT
CGGAATCTTGTTCGGCAGGTGGCTCGGTTCGCTCGCCGTCGGACATGGCCCGATCGTCGCAC
CCGGCAGAGATGGAAGGATGGCGGGTGACGAATACGGCCATCCGCTCGGGGATCGACCTG
AGCCATGTCGACGACAGCATCCGCCCGCAAGACGACCTGTTCGGTCACGTCAACGGCCGCTG
GCTGGCCGAATACGAGATACCCGCCGACCGGGCCACCGACGGCGCCTTCCGGCAGCTCTAC
GACCGCGCCGAGGAGCAGGTGCGCGACCTGATCGTCGAGGCCAGCGAGCAGGGTGCGGCCG
CCGGCGGTGACGACGCCCAACGCATCGGCGACCTGTACGCCAGCTTCCTGGACGAGGACAC
CGTGCAGCGCCGCGGCCTGCAGCCCCTGCTCGACGAGCTGGCGCTCATCGACGAGGCCGCC
GACGCCGCCGCCCT

What is claimed is:

1. A method for differentially detecting a non-*Mycobacterium avium* subsp. *paratuberculosis* (non-MAP) *Mycobacterium Avium* Complex (MAC) organism selected from the group consisting of *Mycobacterium avium* subsp. *Avium* (MAA), *Mycobacterium avium* subsp *silvaticum* (MAS), and *Mycobacterium* subsp *hominissuis* (MAH), from a *Mycobacterium avium* subsp. *paratuberculosis* (MAP) organism comprising:
   amplifying from a sample at least one non-MAP-specific target nucleic acid selected from the group consisting of SEQ ID NO:1, SEQ ID. NO: 2, SEQ ID NO: 3, SEQ ID NO: 4, SEQ ID NO: 5, SEQ ID NO: 6, SEQ ID NO: 7, SEQ ID NO: 8, and full complements thereof, comprising contacting nucleic acids from the sample with at least one primer set that can hybridize to and amplify the at least one non-MAP-specific target nucleic acid, under conditions suitable for amplification; and
   detecting an amplified nucleic acid, wherein detecting the amplified nucleic acid is indicative of the presence of a non-MAP MAC organism in the sample.

2. The method of claim 1, wherein the at least one primer set consists of a forward primer and a reverse primer selected from: SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; and full complements thereof.

3. The method of claim 2, wherein the step of detecting an amplified nucleic acid comprises hybridizing a probe that can reveal the presence of the amplified nucleic acid.

4. The method of claim 3, wherein the probe is selected from SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, and SEQ ID NO: 47, full complements thereof, and labeled derivatives thereof, wherein the label is selected from a dye, a radioactive isotope, a chemiluminescent label, an enzyme, a fluorescein dye, a rhodamine dye, a cyanine dye and combinations thereof.

5. The method of claim 2, further comprising using at least two primer sets, each primer set having one forward primer and one reverse primer, that can hybridize to and amplify the non-MAP-specific target nucleic acid, under conditions suitable for amplification; and detecting at least two amplified nucleic acids, wherein detecting at least two amplified nucleic acids indicates the presence of a non-MAP MAC organism in the sample.

6. The method of claim 1, wherein the sample is an veterinary sample, an animal sample, a food sample, an agricultural sample, a produce sample, a clinical sample, an environmental sample, a biological sample, a water sample or an air sample.

7. The method of claim 6, wherein the animal sample is obtained from a cow, a sheep, a bison, a deer, a pig, or a rabbit.

8. The method of claim 1 further comprising:
   detecting the presence of two of the non-MAP-specific target nucleic acids comprising:
      amplifying from the same sample a second non-MAP specific nucleic acid by contacting nucleic acids present in the sample with at least a second primer set under conditions suitable for a nucleic acid amplification reaction; and
      c) detecting a second amplified nucleic acid.

9. A kit for use in the method of claim 1 comprising:
   at least one primer set having one forward primer and one reverse primer selected from: SEQ ID NO: 9 and SEQ ID NO: 10; or SEQ ID NO: 12 and SEQ ID NO: 13; or SEQ ID NO: 15 and SEQ ID NO: 16; or SEQ ID NO: 18 and SEQ ID NO: 19; or SEQ ID NO: 21 and SEQ ID NO: 22; or SEQ ID NO: 24 and SEQ ID NO: 25; or SEQ ID NO: 27 and SEQ ID NO: 28; or SEQ ID NO: 30 and SEQ ID NO: 31; or SEQ ID NO: 33 and SEQ ID NO: 34; or SEQ ID NO: 36 and SEQ ID NO: 37; or SEQ ID NO: 39 and SEQ ID NO: 40; or SEQ ID NO: 42 and SEQ ID NO: 43; or SEQ ID NO: 45 and SEQ ID NO: 46; and full complements thereof;
   at least one probe selected from SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, and SEQ ID NO: 47, full complements thereof, and labeled derivatives thereof, wherein the label is selected from a dye, a radioactive isotope, a chemiluminescent label, an enzyme, a fluorescein dye, a rhodamine dye, a cyanine dye and combinations thereof;
   one or more components selected from a group consisting of: at least one enzyme, dNTPs, at least one buffer, at least one salt, at least one control nucleic acid sample; and
   an instruction protocol.

* * * * *